(12) United States Patent
Dou et al.

(10) Patent No.: US 9,889,112 B2
(45) Date of Patent: Feb. 13, 2018

(54) LOBAPLATIN CRYSTAL, PREPARATION METHOD AND PHARMACEUTICAL APPLICATION

(71) Applicant: Guizhou Yibai Pharmaceutical Company Limited, Guiyang (CN)

(72) Inventors: Qiling Dou, Guiyang (CN); Donghu Sui, Guiyang (CN); Shenggui Zhang, Guiyang (CN)

(73) Assignee: GUIZHOU YIBAI PHARMACEUTICAL COMPANY LIMITED, Guiyang (CN)

( * ) Notice: Subject to any disclaimer, the term of this patent is extended or adjusted under 35 U.S.C. 154(b) by 0 days.

(21) Appl. No.: 15/314,159

(22) PCT Filed: Nov. 28, 2014

(86) PCT No.: PCT/CN2014/092571
§ 371 (c)(1),
(2) Date: Nov. 28, 2016

(87) PCT Pub. No.: WO2015/192606
PCT Pub. Date: Dec. 23, 2015

(65) Prior Publication Data
US 2017/0189367 A1  Jul. 6, 2017

(30) Foreign Application Priority Data

Jun. 20, 2014 (CN) .......................... 2014 1 0279331
Jun. 20, 2014 (CN) .......................... 2014 1 0279369
Jun. 20, 2014 (CN) .......................... 2014 1 0279879

(51) Int. Cl.
*A61K 31/282* (2006.01)
*C07F 15/00* (2006.01)

(52) U.S. Cl.
CPC ........ *A61K 31/282* (2013.01); *C07F 15/0013* (2013.01)

(58) Field of Classification Search
CPC ................................................... A61K 31/282
(Continued)

(56) References Cited

FOREIGN PATENT DOCUMENTS

CN        1120046 A      4/1996
CN       102020679 A     4/2011

OTHER PUBLICATIONS

International Search Report and Written opinion issued in PCT/CN2014/092571 dated Mar. 5, 2015 (English translation).

*Primary Examiner* — Taofiq A Solola
(74) *Attorney, Agent, or Firm* — Swanson & Bratschun, L.L.C.

(57) ABSTRACT

The present invention relates to new crystals A, B and F of lobaplatin as well as preparation methods therefor and pharmaceutical applications thereof. Lobaplatin crystal A has a melting point Tm.p. of 220±5° C. and is obtained by adding a lobaplatin trihydrate to a suspension crystallization solvent. Lobaplatin crystal B has a melting point $T_{m.p.}$ of 230±5° C. and is obtained by performing solvent evaporation on a lobaplatin trihydrate or by adding a solvent to a lobaplatin dihydrate, and performing room temperature evaporation or solventing-out crystallization and then drying. Lobaplatin crystal F has a melting point Tm.p. of 229±5° C. and is obtained by adding methanol or ethanol to a lobaplatin dihydrate, stirring at room temperature until solids are dissolved, filtering out insolubles, slowly adding an organic solvent, crystallizing out, separating the crystal and drying the crystal. Compared with the existing lobaplatin and lobaplatin trihydrate, the lobaplatin crystals A, B and F have better stability and solubility, are more suitable for preparation of various forms of pharmaceutical preparations, (Continued)

are more suitable for storage and use, and can be better used for treating cancers such as breast cancer, small cell lung cancer, or chronic myeloid leukemia.

7 Claims, 7 Drawing Sheets

(58) Field of Classification Search
USPC .......................................................... 549/206
See application file for complete search history.

LOBAPLATIN CRYSTAL, PREPARATION METHOD AND PHARMACEUTICAL APPLICATION

RELATED APPLICATIONS

This application is a 35 U.S.C. § 371 national phase application of International Application Serial No. PCT/CN2014/092571 (WO2015/192606), filed on Nov. 28, 2014, entitled "Lobaplatin Crystals, Preparation Methods And Pharmaceutical Application". International Application Serial No. PCT/CN2014/092571 claims priority to Chinese Serial No. 201410279369.0, filed Jun. 20, 2014; Chinese Serial No. 201410279879.8, filed Jun. 20, 2014; and Chinese Serial No. 201410279331.3, filed Jun. 20, 2016, each of which are incorporated herein by reference in their entirety.

TECHNICAL FIELD

The present invention relates to a field of pharmaceuticals, especially to new crystals of lobaplatin, preparation methods thereof and pharmaceutical applications thereof, which belong to the technical field of medicines.

BACKGROUND ART

Lobaplatin (D19466), is the third generation platinum antitumor drugs following cisplatin and carboplatin, with chemical name of cis-[trans-1,2-cyclobutane bis (methylamine)-N, N']-[(2S)-lactate-O1, O2]-platinum (II), a molecular formula of $C_9H_{18}N_2O_3Pt$, a molecular weight of 397.34, and a chemical structural formula shown in formula (1) as follows:

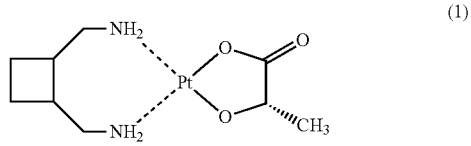

(1)

Lobaplatin belongs to an alkylating agent (generalized) with an alkanisation function. Besides, it has good anti-tumor activity, for example, it has strong inhibition effect on AH135-tumor in vitro, B16-melanoma, colon 115, P338 leukemia of the mouse in vivo etc. The lobaplatin has the characteristics of strong anti-cancer activity, low toxicity, without cumulative toxicity and nephrotoxicity, furthermore, low toxicity for bone marrow and without thrombocytopenia. Lobaplatin for injection existing on the market is mainly used for the treatment of breast cancer, small-cell lung cancer and chronic myelogenous leukemia.

The original prescription of this drug belongs to the ASTA Pharmaceutical Co., Ltd. of German (ASTA Medica AG), of which a preparation method of lobaplatin was described for the first time in the original patent EP0324154. A preparation method of lobaplatin trihydrate was disclosed in subsequent patent EP0611303, and the product is obtained by the recrystallization of anhydrous lobaplatin to form a crystal product containing three water molecules. In the patent EP0611303, it was pointed out that lobaplatin obtained by the preparation method (example 1a) has property of deliquescence, so that the lobaplatin is easy to be sticky and hard to be made into preparations.

SUMMARY OF THE INVENTION

The technical problem to be solved by the present invention lies in that the current anhydrous lobaplatin has the problems of deliquescence, great difficulty to be made into preparations and poor stability. The present invention provides new lobaplatin crystals being very ideal for high bioavailability, good stability, high solubility, good fluidity, difficulty to absorb moisture so as to be sticky, and yield and purity.

A person skilled in the art know that, the same drug having different crystal forms may have differences in bioavailability, as well as stability, flowability, compressibility, etc. These physico-chemical properties can have certain influences on application of drugs. Polymorphism of drugs has become a necessary and important part of the drug research process, quality control and testing process for pharmaceutical production. Researches on the polymorphism of drug is helpful for biological activity chosen from new drug compounds, helpful for improving the bioavailability and strengthening the clinical curative effect, helpful for selection and design of drug administration routes and determination of polytechnic parameters for pharmaceutical preparations, to improve product quality thereby.

Through constant studies and improvements, new lobaplatin crystal forms as well as preparation methods thereof and pharmaceutical applications thereof are invented.

To be specific, in order to solve the technical problems mentioned in the above, the present invention provides the following several kinds of technical solutions of new lobaplatin crystals:

(1) Lobaplatin Dihydrate

Firstly, the present invention provides a lobaplatin dihydrate (also called lobaplatin crystal A), preparation methods thereof and pharmaceutical applications thereof. Detailed descriptions are as follows:

The present invention provides a crystal of lobaplatin compound, being characterized in two molecules of crystal water existing in a crystal structure.

Preferably, a crystal form of said lobaplatin compound of the present invention is crystal A, and there are diffraction peaks at 2θ values of about 11.04, 12.32, 12.61, 13.85, 15.14, 15.55, 16.68, 17.67, 17.86, 19.03, 20.06, 21.00, 22.68, 22.92, 23.76, 25.39, 25.58, 26.37, 26.77, 27.00, 27.71, 28.13, 29.71, 31.42, 31.94, 32.89, 34.29, 34.60, 36.10, 36.93, 37.66, 40.78, 43.41 in a PXRD pattern, wherein an error range of 2θ values is 0.2.

Preferably, a melting point $T_{m.p.}$ of said lobaplatin compound crystal is 220±5° C.

Preferably, the crystal form of said lobaplatin compound crystal is crystal A, which belongs to the orthorhombic system, with the space group of $P2_12_12_1$, unit cell parameters of a=10.601 (2) Å, b=14.020 (3), c=9.759 (2) Å, α=β=γ=90.0°, the unit cell volume of V=1450.5 (5) Å3, and the asymmetric numbers of Z=4 in the unit cell.

On the other hand, the present invention further provides a method of preparing the above mentioned lobaplatin compound, being characterized in comprising the following steps:

adding lobaplatin trihydrate to a solvent for suspension crystallization to form a mixture in suspension state, stirring the mixture, precipitating crystal, removing the solvent, and then drying to get the crystal.

Preferably, in the above mentioned method, after removing the solvent, the crystal is washed with ethyl ether before drying, wherein, said drying is vacuum drying.

Preferably, in the above mentioned method, a ratio of mass of said lobaplatin trihydrate to volume of said crystallization solvent is 1 (g):15-30 (ml).

Preferably, in the above mentioned method, said crystallization solvent is selected from methyl tert-butyl ether, toluene, ethyl ether, butyl acetate, 1,4-dioxane or n-heptane.

Preferably, in the above mentioned method, said suspension state is performed at room temperature, preferably, said suspension state is performed for 45-50 h.

On the other hand, the present invention provides a pharmaceutical composition characterized in that the above mentioned lobaplatin compound is used as an active component.

Preferably, the amount of the lobaplatin crystal in a minimum unit of said pharmaceutical composition is 5 mg, 10 mg or 50 mg.

Preferably, said pharmaceutical composition is any clinically acceptable pharmaceutical dosage form.

Preferably, said dosage form is a lyophilized preparation for injection.

On the other hand, the present invention further provides the use of the above mentioned lobaplatin compound crystal or the above mentioned pharmaceutical composition for the preparation of anti-cancer drugs.

On the other hand, the present invention further provides the use of the above mentioned lobaplatin compound crystal or the above mentioned pharmaceutical composition for the treatment of cancer, specifically for the treatment of one of breast cancer, small-cell lung cancer or chronic myelogenous leukemia.

The present invention further provides the use of the above mentioned lobaplatin crystal form for preparation of pharmaceutical compositions and pharmaceutical preparations.

(2) Lobaplatin Crystal B

Secondly, the present invention provides a lobaplatin crystal B, preparation methods thereof and pharmaceutical applications thereof. Detailed descriptions are as follows:

The present invention provides a lobaplatin compound crystal, being characterized in that crystal form of the lobaplatin compound is crystal form B, and there are diffraction peaks at 2θ values of about 8.25, 9.77, 11.70, 13.13, 15.28, 16.48, 17.22, 17.74, 19.01, 19.56, 22.28, 23.72, 24.04, 24.30, 25.62, 26.20, 28.57, 30.22, 30.61 in a PXRD pattern, wherein an error range of 2θ values is 0.2.

Preferably, a melting point $T_{m.p.}$ of said lobaplatin compound crystal in the present invention is 230±5° C.

Said melting point is measured by DSC, and a heating speed is 10° C./min assessed based on the maximum peak.

On the other hand, the present invention further provides a method of preparing lobaplatin crystal of crystal B, comprising the following steps:

adding anhydrous methanol or anhydrous ethanol into lobaplatin trihydrate to obtain a mixture, stirring the mixture at room temperature until solids are dissolved, removing insolubles from the mixture, evaporating the mixture slowly, precipitating crystal, separating the crystal, and then drying the crystal to obtain white powder which is lobaplatin crystal B.

Preferably, in the above mentioned preparation method, a ratio of mass of said lobaplatin trihydrate to volume of said anhydrous methanol is 1 (g):40-50 (ml); a ratio of said lobaplatin trihydrate to volume of said anhydrous ethanol is 1 (g):80-90 (ml).

On the other hand, the present invention further provides a method of preparing lobaplatin crystal of crystal B, wherein, comprising the following step b):

adding anhydrous methanol to lobaplatin dihydrate to form a mixture, stirring the mixture at room temperature until solids are dissolved, removing insolubles from the mixture, evaporating the mixture slowly, precipitating crystal, separating the crystal, and drying the crystal to obtain white powder which is lobaplatin crystal B.

On the other hand, the present invention further provides a method of preparing lobaplatin crystal of crystal form B, which comprises the following step b):

adding an organic solvent into lobaplatin dihydrate to form a mixture in suspension state, stirring the mixture at room temperature, precipitating crystal, separating the crystal, and drying the crystal to get white powder which is lobaplatin crystal B.

Preferably, in the above mentioned preparation method, the method of preparing said lobaplatin dihydrate comprises the following step a):

adding a solvent for suspension crystallization to lobaplatin trihydrate to form a mixture in suspension state, stirring the mixture, precipitating crystal, washing with ethyl ether after removing the solvent, and then vacuum drying the crystal to obtain the lobaplatin dihydrate crystal.

Preferably, in the above mentioned method, a ratio of mass of said lobaplatin trihydrate to volume of crystallization solvent is 1 (g):15-30 (ml) in step a).

Preferably, in the above mentioned method, said solvent for crystallization is selected from methyl tert-butyl ether, toluene, ethyl ether, butyl acetate, 1,4-dioxane or n-heptane in step a).

Preferably, in the above mentioned method, after separating the crystal, the crystal is washed with ethyl ether before drying the crystal, wherein said drying is vacuum drying in step b).

Preferably, in the above mentioned method, said suspension state is performed at room temperature in step b), preferably, said suspension state is performed for 45-50 h.

Preferably, in the above mentioned method, a ratio of mass of lobaplatin dihydrate to volume of anhydrous methanol is 1 (g):40-50 (ml) in step b).

Preferably, in the above mentioned method, the organic solvent is selected from n-hexane, acetone, ethyl acetate, nitromethane, acetonitrile, tetrahydrofuran, 2-butanone or dichloromethane in said step b), and the ratio of mass of lobaplatin dihydrate to volume of organic solvent is 1 (g):15-30 (ml).

On the other hand, the present invention provides a pharmaceutical composition characterized in that the above mentioned lobaplatin crystal B is used as an active component.

Preferably, the amount of lobaplatin crystal in a minimum unit of said pharmaceutical composition is 5 mg, 10 mg or 50 mg.

Preferably, the form of said pharmaceutical composition is any clinically acceptable pharmaceutical dosage form.

Preferably, said dosage form is a lyophilized preparation for injection.

On the other hand, the present invention further provides the use of the above mentioned lobaplatin crystal or the above mentioned pharmaceutical composition for the preparation of anti-cancer drugs.

On the other hand, the present invention further provides the use of the above mentioned lobaplatin compound crystal or the above mentioned pharmaceutical composition for the treatment of cancer, preferably for the treatment of one of breast cancer, small-cell lung cancer or chronic myelogenous leukemia.

(3) Lobaplatin Crystal F

Thirdly, the present invention provides a lobaplatin crystal F, preparation methods thereof and pharmaceutical applications thereof. Detailed descriptions are as follows:

The present invention provides a lobaplatin compound crystal, being characterized in that crystal form of the compound is crystal F, and there are diffraction peaks at 2θ values of about 8.21, 11.60, 12.99, 15.24, 16.44, 17.11, 17.55, 18.42, 19.01, 19.20, 19.42, 21.81, 22.17, 22.42, 23.33, 23.85, 24.18, 24.40, 24.77, 25.46, 25.98, 26.13, 27.89, 28.42, 29.03, 30.32, 31.17, 31.94, 33.30, 36.20, 37.62, 39.66 in a PXRD pattern, wherein an error range of 2θ values is 0.2.

Melting point $T_{m.p.}$ of said lobaplatin compound crystal is 229±5° C.

Besides, said melting point is measured by DSC, and a heating speed is 10° C./min assessed based on the maximum peak.

On the other hand, the present invention further provides a method of preparing said lobaplatin crystal F, which is characterized in comprising the following step b):

adding methanol or ethanol into lobaplatin dihydrate to obtain a mixture, stirring the mixture at room temperature until solids are dissolved, filtering the mixture to remove insolubles, adding an organic solvent in the mixture slowly, precipating crystal, separating the crystal, and then drying the crystal to obtain white powder which is lobaplatin crystal F.

Preferably, the method of preparing said lobaplatin dihydrate comprises the following step a):

adding a solvent for suspension crystallization to lobaplatin trihydrate to form a mixture in suspension state, stirring the mixture, precipitating crystal from the mixture, washing the crystal with ethyl ether after removing the solvent, and then vacuum drying the crystal to obtain the lobaplatin dihydrate crystal.

Preferably, a ratio of mass said lobaplatin trihydrate to volume of solvent for crystallization is 1 (g):15-30 (ml) in step a).

Preferably, said solvent for crystallization is selected from methyl tert-butyl ether, toluene, ethyl ether, butyl acetate, 1,4-dioxane or n-heptane in step a).

Preferably, in step b), after separating crystal, the crystal is washed with ethyl ether before drying the crystal, wherein, said drying is vacuum dehydration.

Preferably, said organic solvent is selected from ethylene glycol dimethyl ether, n-hexane, ethyl acetate, acetone, nitromethane, acetonitrile, tetrahydrofuran, or methylene chloride in said step b).

Preferably, the ratio of mass of said lobaplatin dihydrate to volume of organic solvent is 1 (g):120-200 (ml) in said step b).

Preferably, the ratio of mass of said lobaplatin dihydrate to volume of methanol is 1 (g):40-50 (ml); the ratio of mass of said lobaplatin dihydrate to volume of ethanol is 1 (g):80-90 (ml).

On the other hand, the present invention provides a pharmaceutical composition characterized in that the above mentioned lobaplatin crystal F is used as an active component.

Preferably, the amount of lobaplatin crystal in a minimum unit of said pharmaceutical composition is 5 mg, 10 mg or 50 mg.

Preferably, the form of said pharmaceutical composition is any clinically acceptable pharmaceutical dosage form.

Preferably, said dosage form is a lyophilized preparation for injection.

On the other hand, the present invention further provides the use of the above mentioned lobaplatin crystal or the above mentioned pharmaceutical composition for the preparation of anti-cancer drugs.

On the other hand, the present invention further provides the use of the above mentioned lobaplatin crystal or the above mentioned pharmaceutical composition for the treatment of cancer, preferably for the treatment of one of breast cancer, small-cell lung cancer or chronic myelogenous leukemia.

The raw material of lobaplatin trihydrate used in the present invention is prepared according to the method of examples in the patent EP0611303.

The above mentioned lobaplatin crystal is used as an active component in the said pharmaceutical composition, and the amount of lobaplatin crystal in the minimum unit of said pharmaceutical composition is 5 mg, 10 mg or 50 mg. New lobaplatin crystal can be prepared to be a pharmaceutical composition with one or more pharmaceutically acceptable carriers or excipients. Furthermore, said pharmaceutical composition can be prepared into any pharmaceutically acceptable dosage forms clinically suitable for the material, including non gastrointestinal administration dosage forms such as injectable formulation, transdermal formulation, respiratory dosage forms, mucosal administration formulations by cavity and other parts of the body, etc, preferably a lyophilized powder for injection.

The pharmaceutical carriers or excipients may be selected from one or more of: water for injection, mannitol, lactose, polyethylene glycols, polysorbate 80, propylene glycol, tartaric acid, citric acid, ascorbic acid, disodium edetate, calcium disodium edetate, sodium bisulfite, glucose, sodium chloride, soybean oil, soybean lecithin, egg yolk phospholipids, distearoyl phosphatidyl ethanolamine, dextran, glycine, glycerol.

The method of preparing the above mentioned compositions and formulations is generally known to a person skilled in the art. The active form of lobaplatin compounds in the present invention and lobaplatin formulations existing on the market is both the lobaplatin, namely the anhydrous lobaplatin, so the lobaplatin compounds in the present invention apply for treatment of all diseases available in the lobaplatin products existing on the market.

Lobaplatin, namely cis-platinum-[trans-1,2-cyclobutane bis (methylamine)-N, N']-[(2S)-lactate-O1, O2]-platinum (II), belongs to an alkylating agent and a cytotoxic drug, and is also known as a Bioalkylating Agent. Carbonium ions or other compounds having active electrophilic groups can be formed in vivo from the lobaplatin, and can be covalent bound to the groups (such as amino, mercapto, hydroxyl, carboxyl, phosphoric acid group etc.) rich in electrons in the biological macromolecules (DNA, RNA, enzymes) of cells. Because of loss of activities or breakage of DNA molecules thereby, it can result in the death of tumor cells. So the lobaplatin has a strong anti-tumor activity. Pharmacokinetic studies show that, after intravenous injection of lobaplatin, total lobaplatin and free lobplatin as forms have effects on anti-tumor in serums, that is to say, lobaplatin plays an effective role in the form of anhydrous lobaplatin, regardless of the material's status.

The above mentioned three kinds of new crystal forms of lobaplatin of the present invention are developed by conquering defects of easily deliquescence to be sticky, poor stability and not easy to storage etc. of amorphous lobaplatin. The new lobaplatin crystal forms have characteristics of high bioavailability, good stability, not easy to deliquescent etc. Besides, it was unexpectedly found that the new forms of lobaplatin have advantages over lobaplatin trihydrate on high solubility, high yield and purity, and better stability when compared with lobaplatin trihydrate. Therefore, the development of new crystal forms is helpful for selection and design of drug administration routes and the determination of technological parameters for pharmaceutical preparations, so as to improve the quality of drug production. The new lobaplatin compounds of the present invention are very stable at normal temperatures, not easy to deliquescent to be sticky and have good mobility, and compared with amorphous lobaplatin, they have advantage on operability on storages, transportations, and preparations and processings.

EMBODIMENT (1) A First Embodiment of the Present Invention

Figure 1:
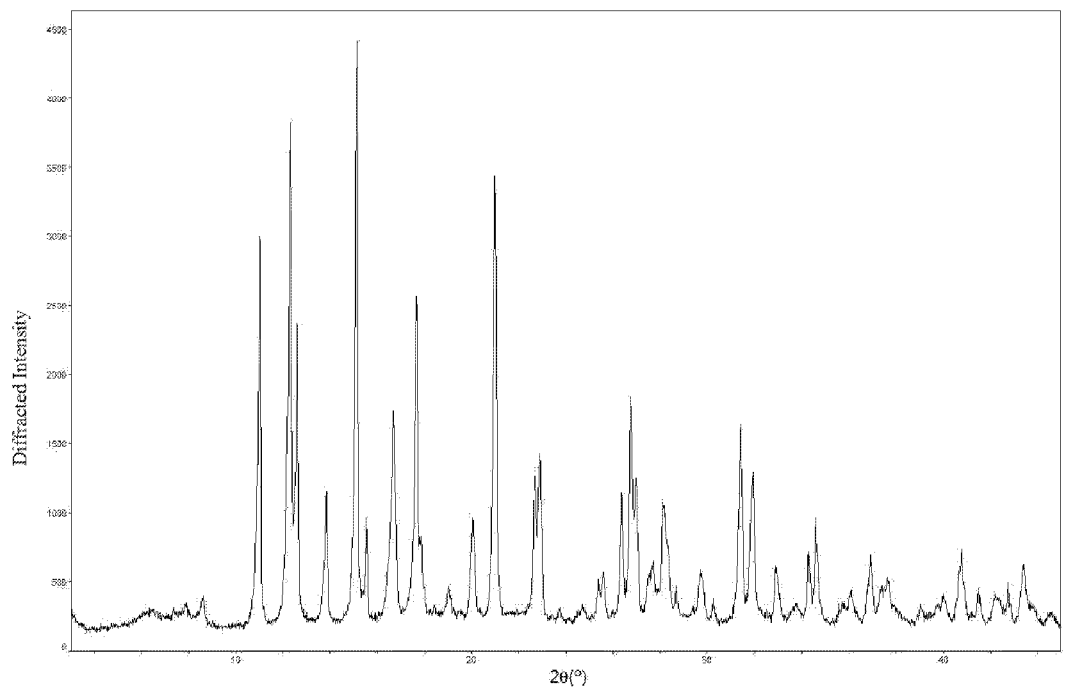
FIG. 1: X-ray diffraction pattern of lobaplatin dihydrate.

The present invention provides a lobaplatin dihydrate having a crystal morphology which has a good solubility, high yield, and excellent stability. Specifically descriptions are shown as follows:

The present invention provides a lobaplatin dihydrate of crystal form A, and its identification datas of the X-ray diffraction (PXRD) are as follows:

The crystal form A of lobaplatin dihydrate is measured by the X-ray diffractometer having the type of Bruker D8 advance XRD manufactured by the Bruker. Measurement conditions are as follows: CuKa (40 kv, 40 mA), a scan rate of 2°/min (2θ values), a scanning range of 3°-45° (2θ values). The crystal form A of lobaplatin dihydrate has absorption peaks of the following characteristics shown in table 1-a, and its diffraction pattern is shown in FIG. 1.

TABLE 1-a the X-ray diffraction (PXRD) measurement result of the crystal form A of lobaplatin dihydrate

| numbers of peaks | diffraction angles 2θ values (approximately) | interplanar distances d (approximately) | relative intensity (approximately) |
| --- | --- | --- | --- |
| 1 | 11.04 | 8.01 | 66.9 |
| 2 | 12.32 | 7.18 | 86.3 |
| 3 | 12.61 | 7.01 | 51.3 |
| 4 | 13.85 | 6.39 | 22.2 |
| 5 | 15.14 | 5.85 | 100 |
| 6 | 15.55 | 5.69 | 17.4 |
| 7 | 16.68 | 5.31 | 35 |
| 8 | 17.67 | 5.02 | 54.5 |
| 9 | 19.03 | 4.66 | 4.8 |
| 10 | 20.06 | 4.42 | 16.8 |
| 11 | 21.00 | 4.23 | 75.9 |

TABLE 1-a-continued the X-ray diffraction (PXRD) measurement result of the crystal form A of lobaplatin dihydrate

| numbers of peaks | diffraction angles 2θ values (approximately) | interplanar distances d (approximately) | relative intensity (approximately) |
| --- | --- | --- | --- |
| 12 | 22.68 | 3.92 | 25.4 |
| 13 | 22.92 | 3.88 | 28.2 |
| 14 | 23.76 | 3.74 | 2 |
| 15 | 25.58 | 3.48 | 7.8 |
| 16 | 26.77 | 3.33 | 37.4 |
| 17 | 27.00 | 3.30 | 22.9 |
| 18 | 27.71 | 3.22 | 8.3 |
| 19 | 28.13 | 3.17 | 19.2 |
| 20 | 29.71 | 3.00 | 8.4 |
| 21 | 31.42 | 2.84 | 33.5 |
| 22 | 31.94 | 2.80 | 25.1 |
| 23 | 32.89 | 2.72 | 8.9 |
| 23 | 34.60 | 2.59 | 17.3 |
| 25 | 36.93 | 2.43 | 10.3 |
| 26 | 37.66 | 2.39 | 7.3 |
| 27 | 40.78 | 2.21 | 12.3 |
| 28 | 43.41 | 2.08 | 9.8 |

The lobaplatin compound of crystal form A is colorless and transparent columnar by performing X-ray single diffraction experiments. The lobaplatin compound of crystal A belongs to the orthorhombic syngony, with the space group of P2₁2₁2₁, unit cell parameters of a=10.601 (2), b=14.020 (3), c=9.759 (2) Å, α=β=γ=90.0°, the unit cell volume of V=1450.5 (5) Å3, and the asymmetric numbers of Z=4 in the unit cell.

The diffraction intensity datas are collected by Bruker SMART APEX-II diffractometer, with parameters of CuKα radiation, graphite monochromator, a single vessel diameter of φ=0.50 mm, a distance between the crystal and CCD detector of d=60.3 mm, a tube voltage of 40 kV, a tube current of 30 mA, a scanning mode of φ/ω scan. The number of total diffraction points collected is 5844, of which number of independent diffraction points is 2376, and the number of observable points is 2376 (|F|2≥2σ|F|2).

The crystal structure is analyzed by direct method (Shelxs97), and all positions of 17 non-hydrogen atoms can be obtained. The structural parameters are amended and the atomic species are determined by the least square method. Positions of all the hydrogen atoms are obtained by the geometric calculation method and difference Fourier method. Ultimately reliable factor R1=0.0569, wR2=0.1491 (w=1/σ|F|2), S=1.077. At last a stoichiometric formula of $C_9H_{18}N_2O_3Pt \cdot 2H_2O$ is determined, with a calculated molecular weight of 433.36 and a calculated crystal density of 1.975 g/cm³. The prepared new lobaplatin crystal is lobaplatin dihydrate determined by structural analyses, with a molecular structure shown in the following formula (2):

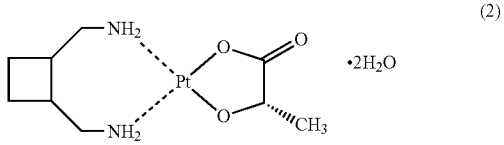

(2)

Figure 2:
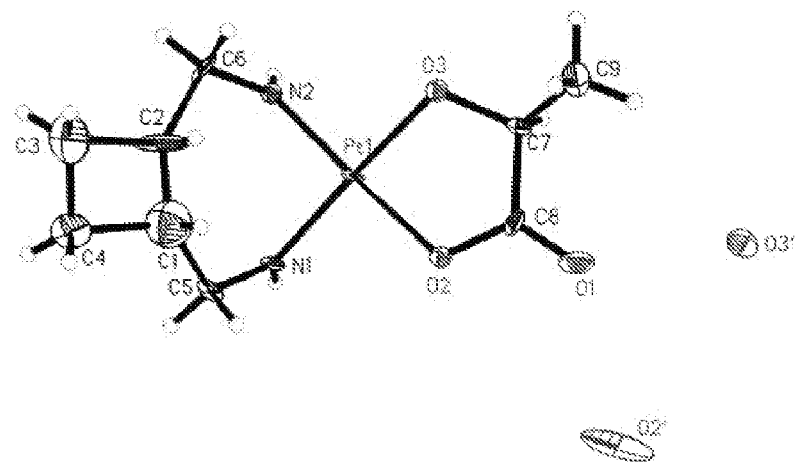
FIG. 2: Projection drawing for molecular stereochemical structure of lobaplatin dihydrate.

A projection drawing for the molecular stereochemical structure of lobaplatin dihydrate of crystal form A is shown in FIG. 2.

Figure 3:
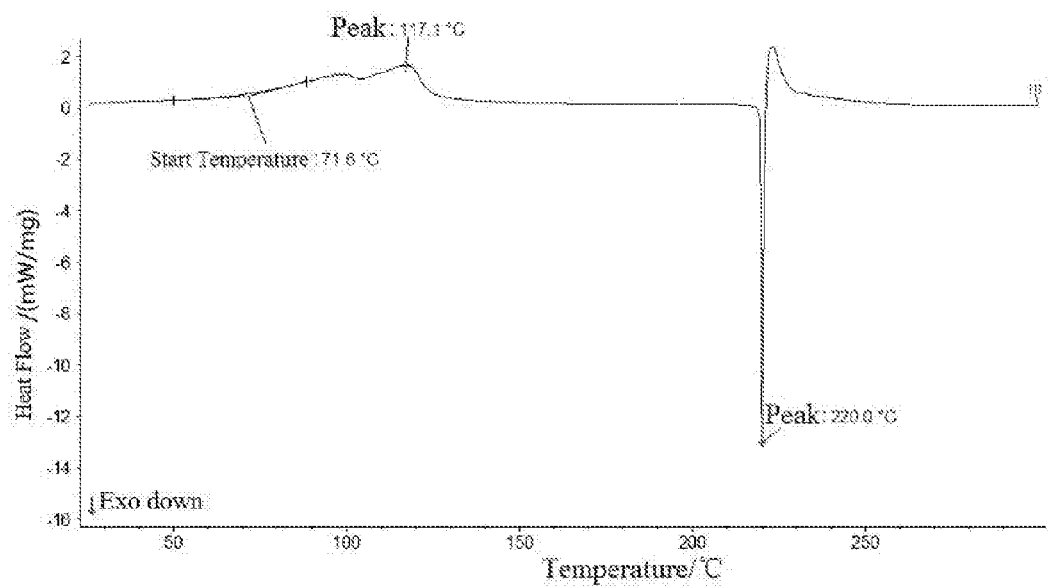
FIG. 3: Differential thermal analysis (DSC pattern) of lobaplatin dihydrate.
Figure 4:
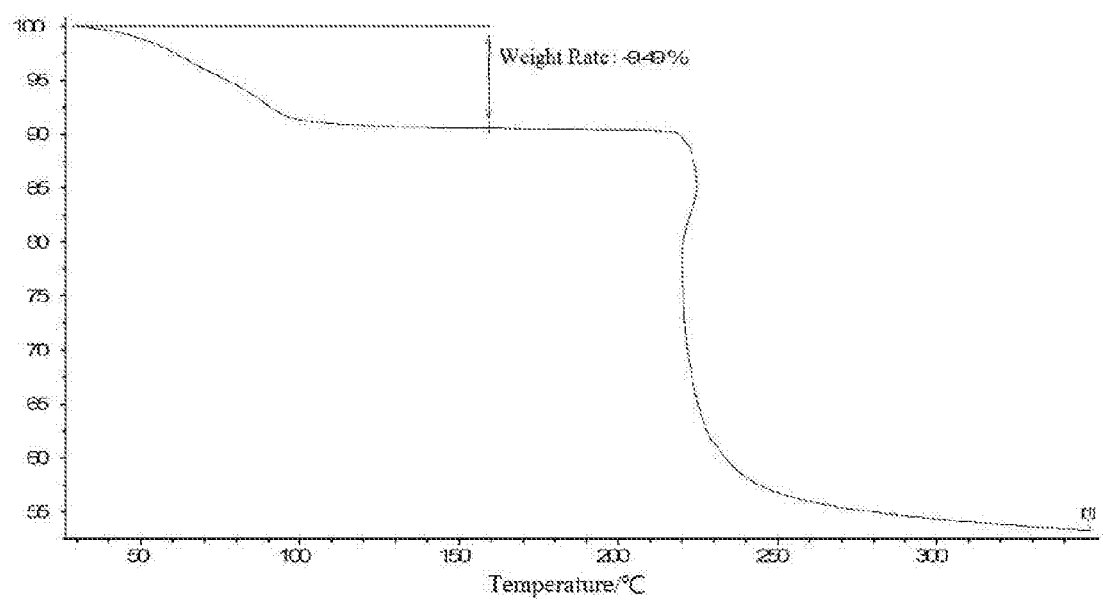
FIG. 4: Thermogravimetic analysis (TGA pattern) of lobaplatin dihydrate.

The differential thermal analysis (DSC-TGA) for the lobaplatin dihydrate of crystal form A is performed by the differential thermal analyzers having models of NETZSCH DSC 204 F1, NETZSCH TG 209 F1 which are manufactured by NETZSCH. The DSC pattern is shown in FIG. 3, and the TGA pattern is shown in FIG. 4. The results show that, measured by the DSC and assessed by the maximum peak, the melting point of $T_{m.p.}$ is 220±5° C. and the heating rate is 10° C./min. Specifically, there is a broad endothermal peak near 117° C. in the DSC pattern. This peak may be produced by the loss of two crystal water judged by combining with the single crystal data and TGA data. There is an exothermal peak at 220±5° C. in the DSC pattern. This is the melting and decomposition peak judged by combining TGA datas and the melting point data recorded in the European Patent EP 0611303. There is 9.49% weight loss in the TGA pattern before 150° C., which indicates that the weight loss is produced by the loss of two crystal water.

On the other hand, the present invention provides a method of preparing the new crystal form A of lobaplatin which is simple to prepare, easy to operate and suitable for an enlarged production, comprising the following steps:

weighting and putting lobaplatin trihydrate in a container, adding an organic solvent to the container to form a mixture in suspension state, stirring the mixture at room temperature for 45-50 h, filtering the mixture, washing the product obtained by filtering with ethyl ether, and then vacuum drying to obtain white powders are obtained which is the lobaplatin dihydrate. The organic solvent is selected from methyl tert-butyl ether, toluene, ethyl ether, butyl acetate, 1,4-dioxane, or n-heptane. The ratio of mass of lobaplatin trihydrate to volume of organic solvent is 1:15-30.

(2) A Second Embodiment of the Present Invention

The present invention provides a new crystal of lobaplatin named crystal form B which has a good solubility and an excellent stability.

Figure 5:
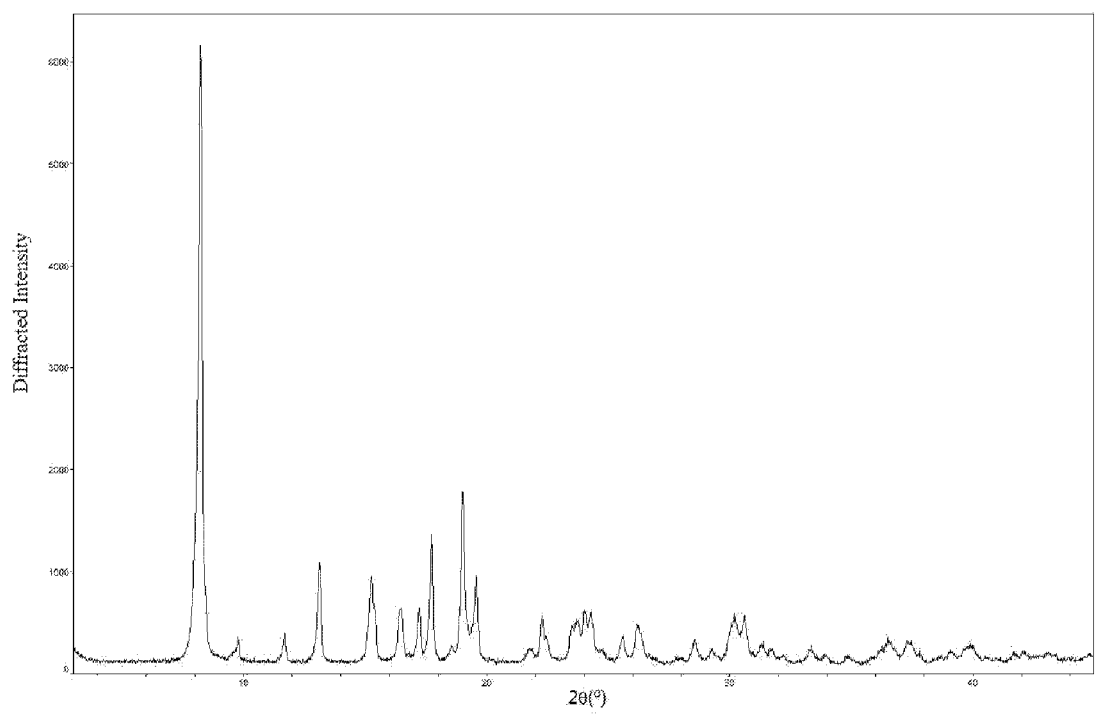
FIG. 5: X-ray diffraction pattern of lobaplatin crystal B.

On the one hand, the present invention provides a lobaplatin crystal B which has a crystal morphology of B. The specific descriptions of prepared crystal form B of lobaplatin in the present invention are shown as follows:

The crystal form B of lobaplatin is measured by a X-ray diffractometer having a model of Bruker D8 advance XRD which is manufactured by the Bruker. Measurement conditions are given as follows: CuKa (40 kv, 40 mA), a scan rate of 2°/min (2θ values), a scanning range of 3°-45° (2θ values). The crystal form B of lobaplatin has absorption peaks of the following characteristics shown in table 1-b, and its diffraction pattern is shown in FIG. 5:

TABLE 1-b

Measurement results of the crystal form B of lobaplatin by the X-ray diffraction (PXRD)

| numbers of peaks | diffraction angle 2θ values (approximately) | interplanar distance d (approximately) | relative intensity (height, approximately %) |
|---|---|---|---|
| 1 | 8.25 | 10.71 | 100 |
| 2 | 9.77 | 9.04 | 3.6 |
| 3 | 11.70 | 7.55 | 4.7 |
| 4 | 13.13 | 6.74 | 16 |
| 5 | 15.28 | 5.80 | 13.7 |
| 6 | 16.48 | 5.37 | 8 |
| 7 | 17.22 | 5.15 | 8 |
| 8 | 17.74 | 4.99 | 20.2 |
| 9 | 19.01 | 4.66 | 27.4 |
| 10 | 19.56 | 4.53 | 14.1 |
| 11 | 22.28 | 3.99 | 7.4 |
| 12 | 23.72 | 3.75 | 6.1 |

TABLE 1-b-continued

Measurement results of the crystal form B of lobaplatin by the X-ray diffraction (PXRD)

| numbers of peaks | diffraction angle 2θ values (approximately) | interplanar distance d (approximately) | relative intensity (height, approximately %) |
|---|---|---|---|
| 13 | 24.04 | 3.70 | 8 |
| 14 | 24.30 | 3.66 | 7.5 |
| 15 | 25.62 | 3.47 | 3.6 |
| 16 | 26.20 | 3.40 | 5.9 |
| 17 | 28.57 | 3.12 | 3.3 |
| 18 | 30.22 | 2.96 | 7.1 |
| 19 | 30.61 | 2.92 | 6.7 |

Figure 6:
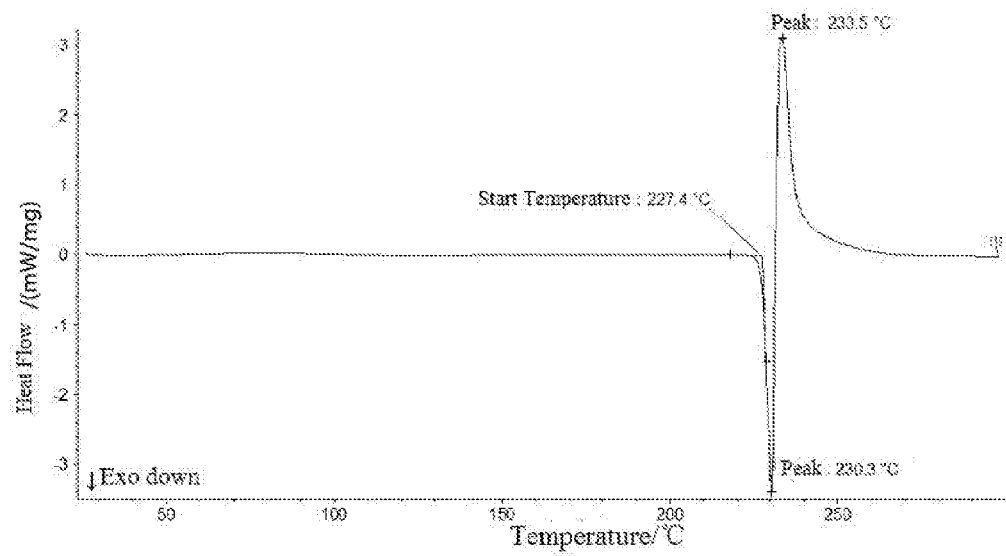
FIG. 6: Differential thermal analysis (DSC pattern) of lobaplatin crystal B.
Figure 7:
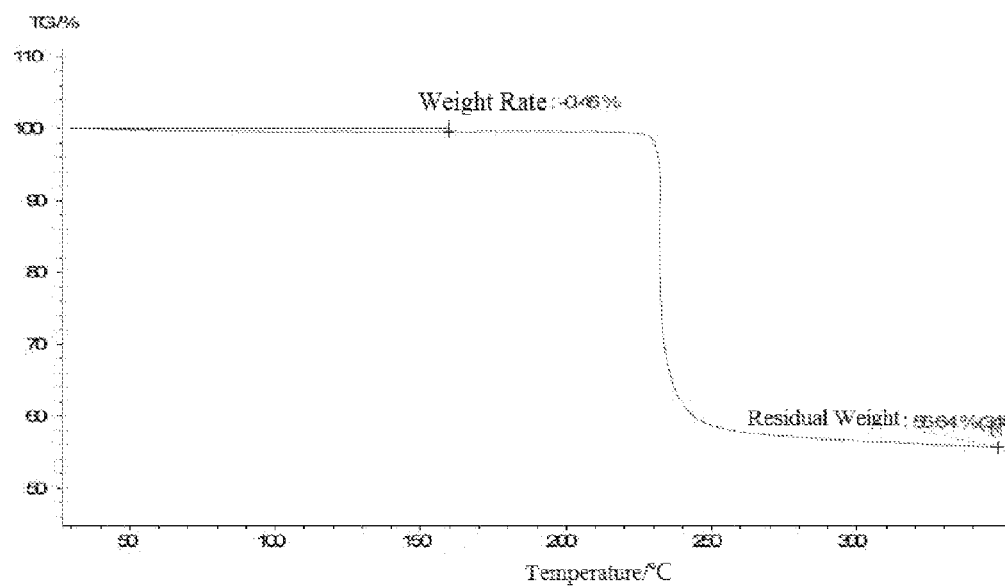
FIG. 7: Thermogravimetic analysis (TGA pattern) of lobaplatin crystal B.

The differential thermal analysis (DSC-TGA) of the new crystal form B of lobaplatin is performed by the differential thermal analyzers having models of NETZSCH DSC 204 F1, NETZSCH TG 209 F1 which are manufactured by NETZSCH. The DSC pattern is shown in FIG. 6, and the TGA pattern is shown in FIG. 7. The results show that, measured by the DSC and assessed by the maximum peak, the melting point of $T_{m.p.}$ is 230±5° C. and the heating rate is 10° C./min. Specifically, there is an exothermal peak at 230±5° C. in the DSC pattern which is the melting and decomposition peak judged by combining TGA datas and the melting point datas recorded in the European Patent EP0611303. There is no weight loss in the TGA pattern before 150° C., which indicates that the lobaplatin crystal form B is the non-solvate.

On the other hand, the present invention provides a method of preparing the new crystal form B of lobaplatin which is simple to prepare, easy to operate and suitable for an enlarged production.

In a preferred embodiment of the present invention, preparation methods of the said new crystal form B of lobaplatin in the present invention comprise the following steps:

a. preparations of lobaplatin dihydrate: weighting and putting lobaplatin trihydrate in a container, adding 15-30 ml of organic solvent with respect to per 1 g of lobaplatin trihydrate to the container to form a mixture in suspension state, stirring the mixture at room temperature for 45-50 h, filtering the mixture, washing the product obtained by filtering with ethyl ether, and then vacuum drying to obtain white powders which is the lobaplatin dihydrate;

wherein, the organic solvent is selected from methyl tert-butyl ether, toluene, ethyl ether, butyl acetate, 1,4-dioxane or n-heptane;

b. preparations of the target crystal: weighting the obtained lobaplatin dihydrate in step a, putting the weighted lobaplatin dihydrate in a container, adding anhydrous methanol to the container, stirring at room temperature until solids are dissolved, filtering to remove insolubes, evaporating slowly in a ventilated kitchen and, separating crystal after precipitation of the crystal, washing the crystal 2-3 times with ethyl ether, and then vacuum drying the crystal to obtain white powders which is the new crystal form B of lobaplatin.

The ratio of mass of lobaplatin dihydrate to volume of anhydrous methanol is 1:40-50 in said step b.

In another preferred embodiment, preparation methods of the said new crystal form B of lobaplatin preferably in the present invention can also be that:

a. preparations of Lobaplatin dihydrate: weighting and putting lobaplatin trihydrate in a container, adding 15-30 ml of organic solvent with respect to per 1 g of lobaplatin trihydrate to the container to form a mixture in suspension state, stirring the mixture at room temperature for 45-50 h, filtering the mixture, washing the product obtained by filtering with ethyl ether, and then vacuum drying to obtain white powders which is the lobaplatin dihydrate;

wherein, the organic solvent is selected from methyl tert-butyl ether, toluene, ethyl ether, butyl acetate, 1,4-dioxane or n-heptane;

b. preparations of the target crystal: weighting the obtained lobaplatin dihydrate in step a, putting the weighted lobaplatin dihydrate in a container, adding an organic solvent to the container to form a mixture in suspension state, stirring at room temperature for 45-50 hours, precipitating crystal, filtering and separating the crystal, washing the crystal 2-3 times with ethyl ether, and then vacuum drying to obtain white powders which is the new crystal form B of lobaplatin.

The said organic solvent in step b is selected from n-hexane, acetone, ethyl acetate, nitromethane, acetonitrile, tetrahydrofuran, 2-butanone or dichloromethane. The ratio of mass of lobaplatin dihydrate to volume of organic solvent is 1:15-30.

In yet another preferred embodiment, preparation methods of the said new crystal form B of lobaplatin preferably in the present invention can also be that: adding anhydrous methanol or anhydrous ethanol into lobaplatin trihydrate, stirring at room temperature until solids are dissolved, removing insolubles, evaporating slowly, separating crystal after precipitation of the crystal, drying to obtain white powders which is the crystal form B of lobaplatin. The ration of mass of lobaplatin trihydrate to volume of anhydrous ethanol is 1:80-90.

(3) A Third Embodiment of the Present Invention

The present invention provides a new crystal of lobaplatin named crystal form F which has a good solubility and an excellent stability.

Figure 8:
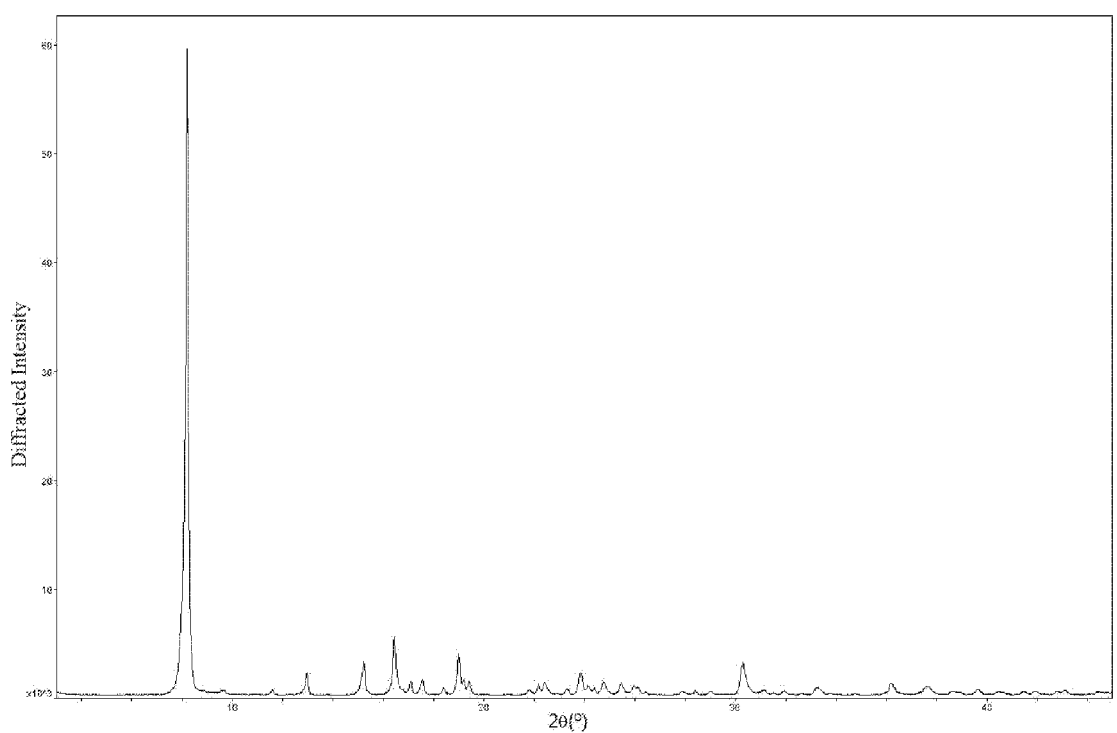
FIG. 8: X-ray diffraction pattern of lobaplatin crystal F.

On the one hand, the present invention provides a lobaplatin crystal F which has a morphology of crystal form F. Then the specific descriptions of the prepared crystal form F of lobaplatin in the present invention are shown as follows:

The crystal form F of lobaplatin is measured by a X-ray diffractometer having the model of Bruker D8 advance XRD which is manufactured by the Bruker. Measurement conditions are given as follows: CuKa (40 kv, 40 mA), a scan rate of 2°/min (2θ values), a scanning range of 3°-45° (2θ values). The crystal form F of lobaplatin has absorption peaks of the following characteristics shown in table 1-c, and its diffraction pattern is shown in FIG. 8:

TABLE 1-c

Measurement results of the crystal form F of lobaplatin by the X-ray diffraction (PXRD)

| numbers of peaks | diffraction angles 2θ values (approximately) | interplanar distance d (approximately) | relative intensity (height, approximately %) |
|---|---|---|---|
| 1 | 8.21 | 10.76 | 100 |
| 2 | 11.60 | 7.62 | 0.8 |
| 3 | 12.99 | 6.81 | 3.3 |
| 4 | 15.24 | 5.81 | 5.2 |
| 5 | 16.44 | 5.39 | 8.9 |
| 6 | 17.11 | 5.18 | 2 |
| 7 | 17.55 | 5.05 | 2.2 |
| 8 | 18.42 | 4.81 | 0.9 |
| 9 | 19.01 | 4.67 | 6.3 |

TABLE 1-c-continued

Measurement results of the crystal form F of lobaplatin by the X-ray diffraction (PXRD)

| numbers of peaks | diffraction angles 2θ values (approximately) | interplanar distance d (approximately) | relative intensity (height, approximately %) |
|---|---|---|---|
| 10 | 19.20 | 4.62 | 2.2 |
| 11 | 19.42 | 4.57 | 2.1 |
| 12 | 21.81 | 4.07 | 0.7 |
| 13 | 22.17 | 4.01 | 1.7 |
| 14 | 22.42 | 3.96 | 1.8 |
| 15 | 23.33 | 3.81 | 0.8 |
| 16 | 23.85 | 3.73 | 3.2 |
| 17 | 24.18 | 3.68 | 1.2 |
| 18 | 24.40 | 3.65 | 0.8 |
| 19 | 24.77 | 3.59 | 1.7 |
| 20 | 25.46 | 3.50 | 1.6 |
| 21 | 25.98 | 3.43 | 1.3 |
| 22 | 26.13 | 3.41 | 1.1 |
| 23 | 27.89 | 3.20 | 0.6 |
| 24 | 28.42 | 3.14 | 0.6 |
| 25 | 29.03 | 3.07 | 0.5 |
| 26 | 30.32 | 2.95 | 4.8 |
| 27 | 31.17 | 2.87 | 0.5 |
| 28 | 31.94 | 2.80 | 0.5 |
| 29 | 33.30 | 2.69 | 1.1 |
| 30 | 36.20 | 2.48 | 1.8 |
| 31 | 37.62 | 2.39 | 1.2 |
| 32 | 39.66 | 2.27 | 0.8 |

Figure 9:
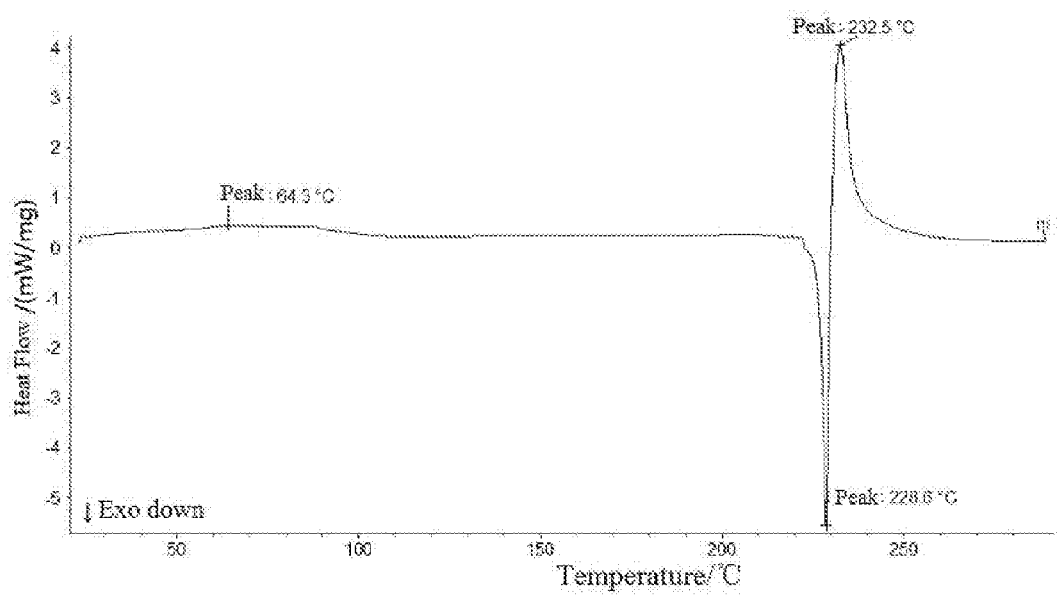
FIG. 9: Differential thermal analysis (DSC pattern) of lobaplatin crystal F.
Figure 10:
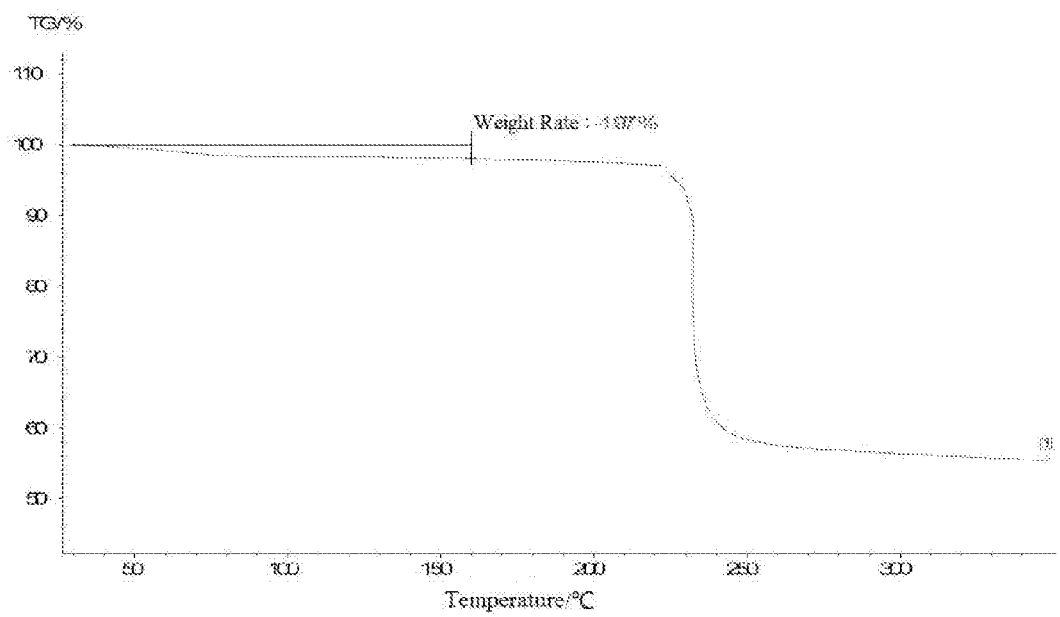
FIG. 10: Thermogravimetic analysis (TGA pattern) of lobaplatin crystal F.

The differential thermal analysis (DSC-TGA) of the new crystal form F of lobaplatin is performed by the differential thermal analyzers having the models of NETZSCH DSC 204 F1, NETZSCH TG 209 F1, which are manufactured by NETZSCH. The DSC pattern is shown in FIG. 9, and the TGA pattern is shown in FIG. 10. The results show that, measured by the DSC and assessed by the maximum peak, the melting point of $T_{m.p.}$ is 229±5° C. and heating rate is 10° C./min. Specifically, there is an exothermal peak at 229±5° C. in the DSC pattern which is the melting and decomposition peak judged by combining TGA datas and the melting point datas recorded in the European Patent EP 0611303. There is 1.97% of weight loss before 150° C. in the TGA pattern, and combining with the DSC datas, it can be concluded that the weight loss is the remained solvent.

On the other hand, the present invention provides a method of preparing the new crystal form F of lobaplatin which is simple to prepare, easy to operate and suitable for an enlarged production.

In a preferred embodiment of the present invention, the methods of preparing the new crystal form F of lobaplatin in the present invention comprise the following steps:

a. preparations of lobaplatin dihydrate: weighting and putting lobaplatin trihydrate in a container, adding 15-30 ml of organic solvent with respect to per 1 g of lobaplatin trihydrate to the container to form a mixture in suspension state, stirring the mixture at room temperature for 45-50 h, filtering the mixture, washing the product obtained by filtering with ethyl ether, and then vacuum drying to obtain white powders which is the lobaplatin dihydrate;

wherein, the organic solvent is selected from methyl tert-butyl ether, toluene, ethyl ether, butyl acetate, 1,4-dioxane or n-heptane;

b. preparations of the target crystal: weighting the obtained lobaplatin dihydrate in step a, putting the weighted lobaplatin dihydrate in a container, adding methanol or ethanol to the container to form a mixture, stirring the mixture at room temperature until solids are dissolved, filtering to remove insolubles, slowly adding an organic solvent to the filter liquid, filtering and separating crystal after precipitation of the crystal, washing the crystal with ethyl ether, and then vacuum drying to obtain white powders which is the new crystal form F of lobaplatin.

The said organic solvent in step b is selected from ethylene glycol dimethyl ether, n-hexane, ethyl acetate, acetone, nitrotoluene, acetonitrile, tetrahydrofuran, dichloromethane. The ratio of mass of lobaplatin dihydrate to volume of organic solvent is 1:120-200.

The ratio of mass of lobaplatin dihydrate to volume of methanol in said step b is 1:40-50, and the ratio of mass of lobaplatin dihydrate to volume of ethanol in said step b is 1:80-90.

EXAMPLES

Preparation methods of Lobaplatin crystal A, B and F in the present invention, as well as screening and separation processes of different new crystal forms and identifications and determinations of properties thereof are described in the following examples specifically in the present invention.

Example 1: Screening and Analyses of Different Crystal Forms 1.1 Screenings Through a Method of Evaporated Crystallization at Room Temperature 20 mg sample of lobaplatin trihydrate was taken into 10 ml volume of vial, and 3 ml of anhydrous ethanol or anhydrous methanol was added in the vial to obtain a mixture. The mixture was evaporated slowly at 25° C. after fully dissolving lobaplatin trihydrate, and dried solids were obtained. The obtained solids were measured by the PXRD. The obtained results were shown in table 2:

TABLE 2

The experiment results of evaporated crystallization at room temperature

| numbers | solvents | PXRD (probably crystal form numbers) |
|---|---|---|
| 1-1 | anhydrous ethanol | B |
| 1-2 | andydrous methanol | B |

The results showed that: by comparison, crystal form obtained from anhydrous methanol was the same crystal form as that of anhydrous ethanol, which was named crystal form B temporarily.

1.2 Screenings Through a Method of Suspension Crystallization 20 mg sample of lobaplatin trihydrate was taken into 10 ml volume of vial, and 4 ml of an organic solvent mentioned in table 3 was added in the vial to prepare a suspension. The prepared suspension is vibrated for 5 h at 25° C., and then the solvent was removed to obtain solids. The obtained solids were measured by PXRD after drying. Results were shown in table 3:

TABLE 3

The experiment results of suspension crystallization

| numbers | solvents | PXRD (probably crystal form numbers) |
|---|---|---|
| 2-1 | toluene | A |
| 2-2 | Para-xylene | A |

TABLE 3-continued

The experiment results of suspension crystallization

| numbers | solvents | PXRD (probably crystal form numbers) |
|---|---|---|
| 2-3 | DMF(N,N-dimethylformamide) | H |
| 2-4 | absolute ethyl ether | A |
| 2-5 | isopropyl ether | A |
| 2-6 | MTBE(methyl tertiary butyl ether) | A |
| 2-7 | n-propyl alcohol | C |
| 2-8 | isopropyl alcohol | I |
| 2-9 | n-butanol | L |
| 2-10 | isobutanol | C |
| 2-11 | benzine | A |
| 2-12 | n-hexane | A |
| 2-13 | cyclohexane | A |
| 2-14 | ethyl acetate | G |
| 2-15 | butyl acetate | A |
| 2-16 | acetone | B |
| 2-17 | 2-butanone | B |
| 2-18 | MIBK(4-methyl-2-pentanone) | G |
| 2-19 | nitromethane | B |
| 2-20 | acetonitrile | B |
| 2-21 | THF(tetrahydrofuran) | B |
| 2-22 | dichloromethane | B |
| 2-23 | DCE(1,2-dichloroethane) | D |
| 2-24 | 1,4-dioxane | A |
| 2-25 | n-heptane | A |
| 2-26 | isopropyl acetate | G |
| 2-27 | sec- butyl alcohol | B |
| 2-28 | DME(dimetoxyethane) | E |

The results showed that: 9 kinds of crystal forms were obtained through the suspension crystallization, which are named crystal form A, B, C, D, E, G, H, I, L temporarily.

1.3 Screenings Through a Method of Dissolution and Precipitation Crystallization A solution was made through adding 20 mg sample of lobaplatin trihydrate to 3 ml of anhydrous methanol or anhydrous ethanol. The following organic solvents were gradually added until solids were precipitated, and then a supernatant was removed to obtain solids. The solids were measured by PXRD after drying. The obtained results were shown in Table 4.

TABLE 4

The experiment results of solvent crystallization

| numbers | good solvents | poor solvents | PXRD (probably crystal form numbers) |
|---|---|---|---|
| 3-1 | anhydrous methanol | toluene | J |
| 3-2 | | absolute ethyl ether | K |
| 3-3 | | MTBE | K |
| 3-4 | | benzine | F |
| 3-5 | | n-hexane | F |
| 3-6 | | cyclohexane | F |
| 3-7 | | ethyl acetate | F |
| 3-8 | | acetone | F |
| 3-9 | | 2-butanone | F |
| 3-10 | | nitromethane | F |
| 3-11 | | acetonitrile | F |
| 3-12 | | THF | F |
| 3-13 | | dichlormethane | F |
| 3-14 | | DCE | K |
| 3-15 | | 1,4-dioxane | M |
| 3-16 | | DME | F |
| 3-17 | anhydrous ethanol | toluene | E |
| 3-18 | | absolute ethyl ether | N |
| 3-19 | | MTBE | K |
| 3-20 | | benzine | F |
| 3-21 | | n-hexane | P |
| 3-22 | | cyclohexane | P |

TABLE 4-continued

The experiment results of solvent crystallization

| numbers | good solvents | poor solvents | PXRD (probably crystal form numbers) |
|---|---|---|---|
| 3-23 | | ethyl acetate | F |
| 3-24 | | acetone | F |
| 3-25 | | 2-butanone | F |
| 3-26 | | nitromethane | no precipitation |
| 3-27 | | acetonitrile | F |
| 3-28 | | THF | K |
| 3-29 | | dichlormethane | K |
| 3-30 | | DCE | O |
| 3-31 | | 1,4-dioxane | M |
| 3-32 | | DME | F |

The results showed that: 7 kinds of crystal forms were obtained through solvent crystallization, which were named crystal form F, J, K, M, N, O, P temporarily.

1.4 Characterization of Different Crystal Forms

In addition to the PXRD measurement to crystal form A-P samples, DCS, and TGA characterization can also be carried out. Names, models and manufacturers of each instruments to be used were shown in Table 5.

TABLE 5

Models and manufacturers of each instruments used to the characterization of crystal forms

| Names of instruments | Models | Manufacturers |
|---|---|---|
| PXRD diffractometer | Bruker D8 advance XRD | Bruker |
| differential thermal analyzer | NETZSCH DSC 204 F1 NETZSCH TG 209 F1 | NETZSCH |
| HPLC analysator | Agilent 1260 Infinity | Agilent |

The measurement results were as follows:

Crystal form A was characterized in that there were diffraction peaks at 2θ values of about 11.04, 12.32, 12.61, 13.85, 15.14, 15.55, 16.68, 17.67, 17.86, 19.03, 20.06, 21.00, 22.68, 22.92, 23.76, 25.39, 25.58, 26.37, 26.77, 27.00, 27.71, 28.13, 29.71, 31.42, 31.94, 32.89, 34.29, 34.60, 36.10, 36.93, 37.66, 40.78, 43.41 in the PXRD pattern, wherein the error range of 2θ values was 0.2;

Crystal form A was characterized in that there was an exothermal peak near 220±5° C. in the DSC pattern.

Crystal form B was characterized in that there were diffraction peaks at 2θ values of about 8.25, 9.77, 11.70, 13.13, 15.28, 16.48, 17.22, 17.74, 19.01, 19.56, 22.28, 23.72, 24.04, 24.30, 25.62, 26.20, 28.57, 30.22, 30.61 in the PXRD pattern, wherein the error range of 2θ values was 0.2.

Crystal form B was characterized in that there was an exothermal peak near 230±5° C. in the DSC pattern.

Crystal form C was characterized in that there were diffraction peaks at 2θ values of about 6.79, 8.07, 12.24, 12.61, 13.50, 16.50, 17.83, 18.32, 18.79, 20.09, 21.64, 22.27, 23.19, 24.73, 27.34, 28.35, 29.12, 31.92 in the PXRD pattern, wherein the error range of 2θ values was 0.2.

Crystal form C was characterized in that there was an exothermal peak near 228±5° C. in the DSC pattern.

Crystal form D was characterized in that there were diffraction peaks at 2θ values of about 6.76, 11.07, 12.35, 12.65, 13.88, 15.18, 15.56, 16.68, 17.70, 17.90, 20.08, 21.02, 22.70, 22.92, 25.41, 25.64, 26.41, 26.79, 27.02, 28.15, 31.44, 31.96, 32.96, 34.34, 34.62, 36.93, 40.82, 43.46 in the PXRD pattern, wherein the error range of 2θ values was 0.2.

Crystal form D was characterized in that there was an exothermal peak near 218±5° C. in the DSC pattern.

Crystal form E was characterized in that there were diffraction peaks at 2θ values of about 6.61, 8.09, 12.38, 13.03, 15.40, 16.66, 17.47, 19.07 in the PXRD pattern, wherein the error range of 2θ values was 0.2;

Crystal form E was characterized in that there was an exothermal peak near 214±5° C. in the DSC pattern.

Crystal form F was characterized in that there were diffraction peaks at 2θ values of about 8.21, 11.60, 12.99, 15.24, 16.44, 17.11, 17.55, 18.42, 19.01, 19.20, 19.42, 21.81, 22.17, 22.42, 23.33, 23.85, 24.18, 24.40, 24.77, 25.46, 25.98, 26.13, 27.89, 28.42, 29.03, 30.32, 31.17, 31.94, 33.30, 36.20, 37.62, 39.66 in the PXRD pattern, wherein the error range of 2θ values was 0.2;

Crystal form F was characterized in that there was an exothermal peak near 229±5° C. in the DSC pattern.

Crystal form G was characterized in that there were diffraction peaks at 2θ values of about 8.62, 10.82, 11.03, 12.26, 12.59, 13.82, 15.12, 15.57, 16.59, 17.43, 17.65, 18.48, 19.46, 20.11, 20.37, 21.01, 22.66, 22.86, 24.60, 25.40, 26.33, 26.77, 27.00, 28.11, 29.79, 31.42, 31.94, 32.87, 34.25, 34.58, 36.06, 40.76, 42.75, 43.39 in the PXRD pattern, wherein the error range of 2θ values was 0.2.

Crystal form H was characterized in that there were diffraction peaks at 2θ values of about 8.35, 8.53, 8.68, 12.97, 15.24, 17.41, 18.40, 19.13, 19.48, 20.37, 24.68, 25.41, 30.33, 31.66, 36.34 in the PXRD pattern, wherein the error range of 2θ values was 0.2.

Crystal form I was characterized in that there were diffraction peaks at 2θ values of about 6.75, 8.39, 11.07, 11.59, 12.32, 12.63, 12.99, 15.20, 16.80, 17.07, 17.57, 19.14, 19.46, 21.00, 22.13, 22.84, 23.29, 23.77, 24.22, 25.82, 26.76, 28.38, 30.34, 30.83, 31.90, 33.63, 36.32, 38.47 in the PXRD pattern, wherein the error range of 2θ values was 0.2.

Crystal form J was characterized in that there were diffraction peaks at 2θ values of about 5.94, 8.35, 9.87, 13.05, 15.28, 16.66, 19.15, 22.22, 22.68, 25.09, 30.71, 33.56 in the PXRD pattern, wherein the error range of 2θ values was 0.2.

Crystal form K was characterized in that there were diffraction peaks at 2θ values of about 8.29, 11.02, 12.31, 12.61, 13.84, 15.14, 15.53, 16.70, 17.66, 19.05, 20.06, 20.98, 22.68, 22.90, 25.60, 26.37, 26.77, 26.98, 27.68, 28.23, 29.75, 31.40, 31.88, 32.90, 33.81, 34.29, 34.60, 36.10, 36.84, 37.64, 39.93, 40.76, 41.51, 42.36, 42.70, 43.39 in the PXRD pattern, wherein the error range of 2θ values was 0.2.

Crystal form L was characterized in that there were diffraction peaks at 2θ values of about 6.71, 7.91, 10.75, 11.84, 14.06, 14.29, 15.85, 16.78, 17.29, 19.76, 20.20, 20.63, 21.08, 21.58, 21.89, 22.17, 23.87, 25.09, 26.83, 27.02, 28.73, 29.18, 29.92, 30.56, 31.61, 33.95, 40.33, 41.33 in the PXRD pattern, wherein the error range of 2θ values was 0.2.

Crystal form M was characterized in that there were diffraction peaks at 2θ values of about 8.05, 13.03, 15.20, 16.19, 17.47, 18.77, 19.32, 24.06 in the PXRD pattern, wherein the error range of 2θ values was 0.2.

Crystal form N was characterized in that there were diffraction peaks at 2θ values of about 7.94, 12.67, 14.83, 16.32, 17.16, 18.71, 21.83, 22.44, 24.10, 24.89, 27.97, 30.02, 30.48 in the PXRD pattern, wherein the error range of 2θ values was 0.2.

Crystal form O was characterized in that there were diffraction peaks at 2θ values of about 6.75, 8.15, 16.29, 18.95, 22.23, 24.52, 29.93 in the PXRD pattern, wherein the error range of 2θ values was 0.2.

Crystal form P was characterized in that there were diffraction peaks at 2θ values of about 6.61, 8.17, 13.34, 16.52, 20.10, 24.97, 27.02, 33.99, 41.06 in the PXRD pattern, wherein the error range of 2θ values was 0.2.

1.5 Repeated and Scaled-Up Experiments 100 mg samples of crystal forms A-P were carried out amplified and repeated trials to test repeatability of crystal forms according to the above-mentioned "1.2 Screenings through a method of suspension crystallization". Results were shown in Table 6 below:

TABLE 6

The results of repeated and scaled-up experiments

| crystal form | numbers | methods | results |
|---|---|---|---|
| A | 4-1 | suspension by cyclohexane, para-xylene or butyl acetate | repeatable |
| B | 4-2 | Suspension by acetone, 2-butanone, nitromethane, acetonitrile or tetrahydrofuran | repeatable |
| C | 4-3 | Suspension by n-propyl alcohol or isobutanol | repeatable |
| D | 4-4 | Suspension by DCE | repeatable |
| E | 4-5 | Suspension by DME | repeatable |
| F | 4-6 | Solvent prepicitation by ethanol-acetone, methanol-acetonitrile | repeatable |
| G | 4-7 | Suspension by MIBK or isopropyl acetate | transformed into crystal form D |
| H | 4-8 | Suspension by DMF | transformed into crystal form B |
| I | 4-9 | suspension by isopropanol | repeatable, difficult to sacle-up |
| J | 4-10 | low yield | unrepeatable |
| K | 4-11 | Solvent prepicitation by methanol-ethyl ether or MTBE | transformed into crystal form F |
| L | 4-12 | suspension by n-butanol | transformed into crystal form B |
| M | 4-13 | Solvent prepicitation by methanol-dioxane | transformed into crystal form F |
| N | 4-14 | Solvent prepicitation by ethanol-ethyl ether | difficult to scale up |
| O | 4-15 | Solvent prepicitation by ethanol-DCE | difficult to scale up |
| P | 4-16 | Solvent prepicitation by ethanol-n-hexane | transformed into crystal form F |

The results showed that: crystal forms A-F were stable. While some of crystal forms G-P had difficulty for enlargement and some had the appearance of crystal transformation phenomenon, which were not suitable for further investigation.

That is to say, the raw materials were conducted crystallization screening through methods of evaporation at normal temperatures, suspension crystallization, and dissolution and precipitation crystallization and so on. The patterns were analyzed after using PXRD for characterization, and it was preliminary determinated that there were 16 kinds of crystal forms A-P may be existed in lobaplatin. After verification by repeated and scaled-up experiments, crystal forms A-F were determined to be relatively stable with better repeatability. While some of other crystal forms were difficult to carry out scaled-up production with lower yield, some were inferred as unstable crystal forms for the appearance of crystal transformation phenomenon. Therefore, crystal form A-F were selected further to conduct comprehensive study.

Example 2: Preparations of a New Lobaplatin Crystal Named Crystal Form a and Properties of the Products Thereof and Comparative Analyses 2.1 Preparations of Lobaplatin Dihydrate Named Crystal Form A Preparation Example 1

1 g of lobaplatin trihydrate were weighed and put in a container, and 15 ml of toluene were added in the container to obtain a suspension. The suspension was stirred at room temperature for 48 h until crystals were precipitated. Crystals were separated by filtration and washed 2-3 times with ethyl ether. At last, 0.85 g of white powders were obtained after vacuum drying which was the lobaplatin dihydrate.

Preparation Example 2

1 g of lobaplatin trihydrate were weighed and put in a container, and 15 ml of ethyl ether were added in the container to obtain a suspension. The suspension was stirred at room temperature for 45 h until crystals were precipitated. The crystals were separated by filtration and washed 2-3 times with ethyl ether. At last, 0.88 g of white powders were obtained after vacuum drying which was the lobaplatin dihydrate.

Preparation Example 3

1 g of lobaplatin trihydrate were weighed and put in a container, and 20 ml of butyl acetate were added in the container to obtain a suspension. The suspension was stirred at room temperature for 50 h until crystals were precipitated. The crystals were separated by filtration and washed 2-3 times with ethyl ether. At last, 0.83 g of white powders were obtained after vacuum drying which was the lobaplatin dihydrate.

Preparation Example 4

1 g of lobaplatin trihydrate were weighed and put in a container, and 25 ml of 1,4-dioxane were added in the container to obtain a suspension. The suspension was stirred at room temperature for 48 h until crystals were precipitated. The crystals were separated by filtration and washed 2-3 times with ethyl ether. At last, 0.90 g of white powders were obtained after vacuum drying which was the lobaplatin dihydrate.

Preparation Example 5

1 g of lobaplatin trihydrate were weighed and put in a container, and 30 ml of n-heptane were added in the container to obtain a suspension. The suspension was stirred at room temperature for 46 h until crystals were precipitated. The crystals were separated by filtration and washed 2-3 times with ethyl ether. At last, 0.87 g of white powders were obtained after vacuum drying which was the lobaplatin dihydrate.

Preparation Example 6

1 g of lobaplatin trihydrate were weighed and put in a container, and 15 ml of methyl tert-butyl ether were added in the container to obtain a suspension. The suspension was stirred at room temperature for 48 h until crystals were precipitated. The crystals were separated by filtration and washed 2-3 times with ethyl ether. At last, 0.92 g of white powders were obtained after vacuum dehydration which was the lobaplatin dihydrate.

The samples prepared according to the above mentioned preparation examples were measured with the XRD diffraction by the method of 1.4 in the above example 1. All the six samples were determined to be the same crystal form, and characteristic peaks were as follows: there were diffraction peaks at 2θ values of about 11.04, 12.32, 12.61, 13.85, 15.14, 15.55, 16.68, 17.67, 17.86, 19.03, 20.06, 21.00, 22.68, 22.92, 23.76, 25.39, 25.58, 26.37, 26.77, 27.00, 27.71, 28.13, 29.71, 31.42, 31.94, 32.89, 34.29, 34.60, 36.10, 36.93, 37.66, 40.78, 43.41 in the PXRD pattern, wherein the error range of 2θ values was 0.2.

| Results of elemental analyses: $C_9H_{18}N_2O_3Pt*2H_2O$ M = 433.36 | | | | |
|---|---|---|---|---|
| Calculated value (%): | C 24.95 | H 5.11 | N 6.46 | Pt 45.01 |
| Measured value (%): | C 24.94 | H 5.08 | N 6.41 | Pt 45.07 |

This crystal form was named as crystal form A.

2.2 Properties Determination for Lobaplatin Crystal Products of Crystal Form a and Comparative Analyses Thereof 1. Test Samples Lobaplatin dihydrate number 1-6 in the present invention: the lobaplatin dihydrate of crystal form A prepared by the method of preparation example 1-6 respectively.

Comparative Sample 1: lobaplatin prepared by the method of example 1a recorded in the Patent EP 0324154, and specific preparation method was given as follows:

3.8 g (0.01 mol) of cis-[trans-1,2-butyl-bis (methylamine)-N, N']-dichloro platinum (II) were suspended in 20 ml water to obtain a mixture, and the mixture was heated to 40° C. 3.39 g (0.02 mol) of silver nitrate were added in the mixture and the mixture was stirred for 1.5 hours. The mixture was left to cool in a refrigerator to precipitate silver chloride. The silver chloride precipitation was then filtered and washed with 10 ml of water. The filtrate was passed through a column containing 100 ml of a basic ion exchanger and washed with 150 ml water. Then the filtrate was dropped into 4.5 g (0.01 mol, 20% aqueous solution) of L-lactic acid. After stirring at room temperature for 3 days, the reaction mixture was concentrated, the residue was dissolved in methanol and stirred to fade with additional of activated charcoal. Then the activated charcoal was filtered and ethyl ether was added to the filtrate. The solid obtained by concentration quickly was amorphous lobaplatin.

Comparative Sample 2: lobaplatin trihydrate prepared according to the method recorded in the example of the Patent EP0611303, and the specific preparation method was given as follows:

3.8 g (0.01 mol) of cis-[trans-1,2-butyl-bis (methylamine)-N, N']-dichloro platinum (II) were suspended in 20 ml water to obtain a mixture, and the mixture was heated to 40° C. 3.39 g (0.02 mol) of silver nitrate were added in the mixture and the mixture was stirred for 1.5 hours. The mixture was left to cool in a refrigerator to precipitate silver chloride. The silver chloride precipitate was then filtered and washed with 10 ml of water. The filtrate was passed through a column containing 100 ml of a basic ion exchanger and washed with 150 ml water. Then the filtrate was dropped into 4.5 g (0.01 mol, 20% aqueous solution) of L-lactic acid. After stirring at room temperature for 3 days, the reaction mixture was concentrated to about 20 ml, and left to cool in a refrigerator for overnight to precipitate crystal. The crystal was then filtered and the filtrate was concentrated and left to cool in a refrigerator for overnight to precipitate crystal again. The crystal was filtered and the filtrate was collected. The crystals were combined and recrystallized from 20 ml of water/acetone (1/1, V/V), and crystal obtained thereby was lobaplatin trihydrate.

2. Morphological Identifications

Comparative Sample 1: Lobaplatin obtained was amorphous;

Comparative Sample 2: There were diffraction peaks at 2θ values of about 6.71, 8.35, 12.89, 15.14, 16.74, 17.45, 19.01, 19.40, 22.07, 22.76, 23.16, 24.30, 25.21, 25.74, 27.08, 30.26, 30.79 in the PXRD pattern by the X-ray diffraction, wherein the error range of 2θ values was less than 0.2. The melting point of this sample was described to be 210° C. (decomposition) in the patent EP0611303.

Samples 1-6 of the crystal form A in the present invention: There were diffraction peaks at 2θ values of about 11.04, 12.32, 12.61, 13.85, 15.14, 15.55, 16.68, 17.67, 17.86, 19.03, 20.06, 21.00, 22.68, 22.92, 23.76, 25.39, 25.58, 26.37, 26.77, 27.00, 27.71, 28.13, 29.71, 31.42, 31.94, 32.89, 34.29, 34.60, 36.10, 36.93, 37.66, 40.78, 43.41 in the PXRD pattern by X-ray diffraction, wherein the error range of 2θ values was less than 0.2. There was a broad endothermal peak near 117° C. in the DSC pattern, and this peak may be produced by the loss of two crystal water judged by combining with single crystal datas and TGA datas. There was an exothermal peak at 220±5° C. which was the melting and decomposition peak judged by combining with TGA datas and the melting point datas recorded in the European patent EP0611303. There was 9.49% weight loss before 150° C. in the TGA pattern, which was produced by the loss of two crystal water. All the datas showed that samples 1-6 had the same crystal form which was lobaplatin dihydrate.

3. The Study of Solubility

Concentrations of 60 μg/ml, 80 μg/ml, 200 μm/ml, 400 μm/ml and 800 μm/ml lobaplatin trihydrate control solutions were prepared to make the standard curve by HPLC method. And the standard curve equation obtained was Y=4.8641X+20.5794, R=0.9998. Sample 6 of lobaplatin dihydrate and comparative sample 2 were prepared to be saturated aqueous solutions (suspensions) respectively. The solutions were vibrated for 6 h in a shaker at 25° C. followed by filtration, and diluted to appropriate multiples to analyze by HPLC. The solubility results were shown in Table 7 as follows:

TABLE 7

Study results of the solubility

| crystal form | sample 6 | comparative sample 2 |
|---|---|---|
| solubility (mg/ml) | 16.7307 | 10.3271 |

The results showed that: the solubility of lobaplatin dihydrate prepared in the present invention was better than that of lobaplatin trihydrate.

4. The Quality Contrast Study of Lobaplatin New Crystal Forms 20 mg of samples 1-6 of lobaplatin dihydrate and comparative samples 1-2 were weighed respectively. Product moistures, impurities contents, contents of active ingredients, and yields were regarded as the indexes to study the product quality and yields. Results were shown in Table 8 below:

TABLE 8

The quality contrast study for lobaplatin dihydrate of crystal form A

| sample | moisture contents (%) | impurities contents (%) | lobaplatin contents (%, calculated on anhydrous lobaplatin) | yields (%) |
|---|---|---|---|---|
| sample 1 | 8.80 | 0.28 | 99.56 | 88.5% |
| sample 2 | 8.87 | 0.22 | 99.72 | 91.6% |
| sample 3 | 8.85 | 0.23 | 99.43 | 86.4% |
| sample 4 | 8.79 | 0.26 | 99.66 | 93.7% |
| sample 5 | 8.83 | 0.22 | 99.77 | 90.6% |
| sample 6 | 8.81 | 0.25 | 99.85 | 95.8% |
| comparative sample 1 | 3.78 | 1.21 | 98.26 | 64% |
| comparative sample 2 | 12.14 | 0.42 | 99.51 | 55% |

The above mentioned results showed that, compared with anhydrous lobaplation and lobaplatin trihydrate, the new lobaplatin crystal A obtained by the present invention had the characteristics of high contents, low impurities, and good yields.

Note 1: A determination method of contents: measured by high performance liquid chromatography: chromatographic conditions were shown as follows: octadecylsilane bonded silica as a filler, a ratio of potassium dihydrogen phosphate solution to acetonitrile of 92:8 as the mobile phase, a detection wavelength of 210 nm, a column temperature of 40° C., numbers of theoretical plates should not less than 1000 calculated on lobaplatin peaks, and separating degree of lobaplatin peaks and impurities peaks should meet requirements. Preparations of the control article solution: 10 mg of lobaplatin trihydrate control article were accurately weighed, and fixed in 50 ml of volumetric flask, diluted with water to the graduation, and shaked well. Preparations of test solutions: 20 mg of sample were accurately weighed respectively and fixed in 100 ml of volumetric flask, diluted with water to the graduation, and shaked well. Measurements and results: 10 μl of control article solutions and sample solutions were precisely measured respectively, and were injected into the liquid chromatograph and the chromatograms were recorded. Calculated based on peak areas by an external standard method, contents were calculated on the anhydrous lobaplatin with a standard range of 97.0%-102%.

Note 2: An examination method of impurities: lobaplatin, 1,2-diaminomethyl cyclobutane (CBMA), lactic acid and other known and unknown impurities were determination by TLC. The Developer:ethanol:chloroform:25% aqueous ammonia:water=53:39:15:1.5 (volume ratio), the TLC plates: silica gel 60 $F^{254}$10×10 TLC plates. The plates were placed in the iodine vapor to coloration with 0.3% of ninhydrin reagent and nitroso-dimethylaniline chromogenic reagent after developing. Impurities of CBMA and the unknown were examined.

Note 3: A determination method of moisture contents: the KarlFischer method was used. A theoretical content of moisture for lobaplatin dihydrate was 8.77%, and a theoretical content of moisture for lobaplatin trihydrate was 11.96%.

5. The Study of Stability

The sample 6 prepared in examples of the present invention and the prepared comparative sample 2 were respectively left to the conditions of a 60° C. oven, a relative humidity of about 95%, and a light stability test container of about 4500 lux illumination (a conventional incubator with the illumination function). The samples were taken out to perform PXRD tests and HPLC analyses after 5 days and 10 days to study the stability of samples under the condition of a high temperature, a high humidity and an illumination. Results were shown in Table 9.

TABLE 9

The evaluation results of stability

| | Experimental conditional | | | | | |
|---|---|---|---|---|---|---|
| | thermo-stability | | wet stability | | light stability | |
| | sample 6 | comparative sample 2 | sample 6 | comparative sample 2 | sample 6 | comparative sample 2 |
| PXRD 5 days | stable | stable | stable | stable | stable | stable |
| PXRD 10 days | stable | relatively stable | stable | Relatively stable | stable | stable |
| HPLC 0 day | 99.854% | 99.513% | 99.854% | 99.513% | 99.854% | 99.513% |
| HPLC 5 days | 99.834% | 99.632% | 99.871% | 99.294% | 99.900% | 99.608% |
| HPLC 10 days | 99.750% | 98.737% | 99.441% | 98.815% | 99.694% | 98.726% |

The above mentioned experiment results showed that, lobplatin in the present invention was the new crystal form which had a higher solubility than lobplatin trihydrate, and yields and purity were ideal. The new lobplatin crystal form had a good stability and no appearance of crystal transformation phenomenon from the results of high temperature, high humidity and illumination study. Active ingredients's contents were superior to lobplatin trihydrate and had no apparent changes according to the HPLC results, indicating that the new lobplatin crystal form in the present invention was more stable than lobplatin trihydrate, not easy deliquescence to be sticky and had a good liquidity.

Example 3: Preparations of New Lobaplatin Crystal Named Crystal Form B and Properties of the Products Thereof and Comparative Analyses 3.1 Preparations of New Lobaplatin Crystal Named Crystal Form B Preparation Example 1 a. Preparations of lobaplatin dihydrate: 2 g of lobaplatin trihydrate were weighed and put in a container, and 30 ml of toluene were added in the container to obtain a suspension. The suspension was stirred for 48 h at room temperature, filtered, and the product obtained by filtering was washed with ethyl ether, and then 1.73 g of white powders were obtained after vacuum drying which was the lobaplatin dihydrate.

b. Preparations of target crystal: 1 g of the lobaplatin dihydrate in step a were weighed and put in a container, and 40 ml of anhydrous methanol were added in the container to obtain a mixture. The mixture was stirred at room temperature until solids were dissolved. The mixture was filtered to remove insolubles, evaporated slowly in fume cupboard until the crystal was precipitated, and then the crystal was filtered and separated. Then the crystal was washed 2-3 times with ethyl ether and 0.74 g of white powders were obtained after vacuum drying which was the new crystal form B of lobaplatin.

Preparation Example 2 a. Preparations of lobaplatin dihydrate: 2 g of lobaplatin trihydrate were weighed and put in a container, and 15 ml of methyl tertiary-butyl ether were added to the container to obtain a suspension. The suspension was stirred for 48 h at room temperature, filtered, and the product obtained by filtering was washed with ethyl ether, and then 1.84 g of white powders were obtained after vacuum drying which was the lobaplatin dihydrate.

b. Preparations of target crystal: 1 g of the lobaplatin dihydrate in step a were weighed and put in a container, and 50 ml of anhydrous methanol were added in the container to obtain a mixture. The mixture was stirred at room temperature until solids were dissolved. The mixture was filtered to remove insolubles, evaporated slowly in fume cupboard until the crystal was precipitated, and then the crystal was filtered and separated. Then the crystal was washed 2-3 times with ethyl ether and 0.76 g of white powders were obtained after vacuum drying which was the new crystal form B of lobaplatin.

Preparation Example 3 a. Preparations of lobaplatin dihydrate: 2 g of lobaplatin trihydrate were weighed and put in a container, and 20 ml of butyl acetate were added to the container to obtain a suspension. The suspension was stirred for 50 h at room temperature, filtered, and the product obtained by filtering was washed with ethyl ether, and then 1.68 g of white powders were obtained after vacuum drying which was the lobaplatin dihydrate.

b. Preparations of target crystal: 1 g of the lobaplatin dihydrate in step a were weighed and put in a container, and 20 ml of n-hexane were added in the container to obtain a suspension. The suspension was stirred for 48 h at room temperature to precipitate crystal. The crystal was filtered and separated. Then the crystal was washed 2-3 times with ethyl ether and 0.75 g of white powders were obtained after vacuum drying which was the new crystal form B of lobaplatin.

Preparation Example 4 a. Preparations of lobaplatin dihydrate: 2 g of lobaplatin trihydrate were weighed and put in a container, and 25 ml of 1,4-dioxane were added in the container to obtain a suspension. The suspension was stirred for 45 h at room temperature, filtered, and the product obtained by filtering was washed with ethyl ether, and then 1.76 g of white powders were obtained after vacuum drying which was the lobaplatin dihydrate.

b. Preparations of target crystal: 1 g of the lobaplatin dihydrate in step a were weighed and put in a container, and 15 ml of acetone were added in the container to obtain a suspension. The suspension was stirred for 48 h at room temperature to precipitate crystal. The crystal was filtered and separated. Then the crystal was washed 2-3 times with ethyl ether and 0.78 g of white powders were obtained after vacuum drying which was the new crystal form B of lobaplatin.

Preparation Example 5 a. Preparations of lobaplatin dihydrate: 2 g of lobaplatin trihydrate were weighed and put in a container, and 30 ml of n-heptane were added in the container to obtain a suspension. The suspension was stirred for 50 h at room temperature, filtered, and the product obtained by filtering was washed with ethyl ether, and then 1.75 g of white powders were obtained after vacuum drying which was the lobaplatin dihydrate.

b. Preparations of target crystal: 1 g of the lobaplatin dihydrate in step a were weighed and put in a container, and 18 ml of ethyl acetate were added in the container to obtain a suspension. The suspension was stirred for 50 h at room temperature to precipitate crystal. The crystal was filtered and separated. Then the crystal was washed 2-3 times with ethyl ether and 0.75 g of white powders were obtained after vacuum drying which was the new crystal form B of lobaplatin.

Preparation Example 6 a. Preparations of lobaplatin dihydrate: 2 g of lobaplatin trihydrate were weighed and put in a container, and 15 ml of ethyl ether were added in the container to obtain a suspension. The suspension was stirred for 48 h at room temperature, filtered, and the product obtained by filtering was washed with ethyl ether, and then 1.78 g of white powders were obtained after vacuum drying which was the lobaplatin dihydrate.

b. Preparations of target crystal: 1 g of the lobaplatin dihydrate in step a were weighed and put in a container, and 25 ml of nitromethane were added in the container to obtain a suspension. The suspension was stirred for 48 h at room temperature to precipitate crystal. The crystal was filtered and separated. Then the crystal was washed 2-3 times with ethyl ether and 0.77 g of white powders were obtained after vacuum drying which was the new crystal form B of lobaplatin.

Preparation Example 7 a. Preparations of lobaplatin dihydrate: 2 g of lobaplatin trihydrate were weighed and put in a container, and 18 ml of methyl tertiary-butyl ether were added in the container to obtain a suspension. The suspension was stirred for 48 h at room temperature, filtered, and the product obtained by filtering was washed with ethyl ether, and then 1.82 g of white powders were obtained after vacuum drying which was the lobaplatin dihydrate.

b. Preparations of target crystal: 1 g of the lobaplatin dihydrate in step a were weighed and put in a container, and 30 ml of tetrahydrofuran were added in the container to obtain a suspension. The suspension was stirred for 46 h at room temperature to precipitate crystal. The crystal was filtered and separated. Then the crystal was washed 2-3 times with ethyl ether and 0.79 g of white powders were obtained after vacuum drying which was the new crystal form B of lobaplatin.

Preparation Example 8 a. Preparations of lobaplatin dihydrate: 2 g of lobaplatin trihydrate were weighed and put in a container, and 25 ml of methyl tertiary-butyl ether were added in the container to obtain a suspension. The suspension was stirred for 46 h at room temperature, filtered, and the product obtained by filtering was washed with ethyl ether, and then 1.83 g of white powders were obtained after vacuum drying which was the lobaplatin dihydrate.

b. Preparations of target crystal: 1 g of the lobaplatin dihydrate in step a were weighed and put in a container, and 15 ml of dichloromethane were added in the container to obtain a suspension. The suspension was stirred for 48 h at room temperature to precipitate crystal. The crystal was filtered and separated. Then the crystal was washed 2-3 times with ethyl ether and 0.76 g of white powders were obtained after vacuum drying which was the new crystal form B of lobaplatin.

Preparation Example 9 a. Preparations of lobaplatin dihydrate: 2 g of lobaplatin trihydrate were weighed and put in a container, and 30 ml of methyl tertiary-butyl ether were added in the container to obtain a suspension. The suspension was stirred for 48 h at room temperature, filtered, and the product obtained by filtering was washed with ethyl ether, and then 1.85 g of white powders were obtained after vacuum drying which was the lobaplatin dihydrate.

b. Preparations of target crystal: 1 g of the lobaplatin dihydrate in step a were weighed and put in a container, and 25 ml of acetonitrile were added in the container to obtain a suspension. The suspension was stirred for 48 h at room temperature to precipitate crystal. The crystal was filtered and separated. Then the crystal was washed 2-3 times with ethyl ether and 0.78 g of white powders were obtained after vacuum drying which was the new crystal form B of lobaplatin.

Preparation Example 10 a. Preparations of lobaplatin dihydrate: 2 g of lobaplatin trihydrate were weighed and put in a container, and 15 ml of methyl tertiary-butyl ether were added in the container to obtain a suspension. The suspension was stirred for 48 h at room temperature, filtered, and the product obtained by filtering was washed with ethyl ether, and then 1.84 g of white powders were obtained after vacuum drying which was the lobaplatin dihydrate.

b. Preparations of target crystal: 1 g of the lobaplatin dihydrate in step a were weighed and put in a container, and 20 ml of 2-butanone were added in the container to obtain a suspension. The suspension was stirred for 48 h at room temperature to precipitate crystal. The crystal was filtered and separated. Then the crystal was washed 2-3 times with ethyl ether and 0.73 g of white powders were obtained after vacuum drying which was the new crystal form B of lobaplatin.

Preparation Example 11

1 g of lobaplatin trihydrate were weighed and put in a container, and 40 ml of anhydrous methanol were added in the container to obtain a mixture. The mixture was stirred at room temperature until solids were dissolved. The mixture was filtered to remove insolubles, and then the mixture was evaporated slowly to precipitate crystal. The crystal was filtered and separated. 0.68 g of white powders were obtained after drying which was the crystal form B of lobaplatin.

Preparation Example 12

1 g of lobaplatin trihydrate were weighed and put in a container, and 85 ml of anhydrous ethanol were added in the container to obtain a mixture. The mixture was stirred at room temperature until solids were dissolved. The mixture was filtered to remove insolubles, and then the mixture was evaporated slowly to precipitate crystal. The crystal was filtered and separated. 0.70 g of white powders were obtained after drying which was the lobaplatin crystal form B.

The samples prepared according to step a) in the above mentioned preparation examples 1-10 were measured with XRD diffraction by the method of 1.4 in the foregoing example 1. All the 10 samples were determined to have the same crystal form which was crystal form A. And the detailed determination datas were the same as these of the foregoing first part of the embodiment which is "a first embodiment of the present invention" and these of the foregoing example 2.

On the other hand, the samples prepared through step b) in the above mentioned preparation examples 1-10 and example 11-12 were measured with XRD diffraction by the method of 1.4 in the foregoing example 1. All the 12 samples were determined to have the same crystal form, and the characteristic peaks were as follows: there were diffraction peaks at 2θ values of about 8.25, 9.77, 11.70, 13.13, 15.28, 16.48, 17.22, 17.74, 19.01, 19.56, 22.28, 23.72, 24.04, 24.30, 25.62, 26.20, 28.57, 30.22, 30.61 in the PXRD pattern, wherein the error range of 2θ values was ±0.2.

This crystal form was named as crystal form B.

3.2 Properties Determination for Products of Crystal Form B and Comparative Analyses Thereof 1. Test Samples Samples 1-12: the crystal form B of lobaplatin compounds prepared by the method of preparation examples 1-12 in example 3 in the present invention respectively.

Comparative sample 1: which was the same as the foregoing sample of comparative sample 1 in part 2.2 of example 2. The lobaplatin prepared by the method of example 1a in the patent EP 0324154, and the specific preparation methods were the same as these of the foregoing comparative sample 1 in part 2.2 of example 2.

Comparative sample 2: it was the same as the foregoing sample of comparative sample 2 in part 2.2 of example 2. The lobaplatin trihydrate was prepared by the method of example in the patent EP 0611303, and the specific preparation methods were the same as these of the foregoing comparative sample 2 in part 2.2 of example 2.

2. Morphological Identifications

The identification results were the same as those of comparative sample 1 and comparative sample 2 in the part 2.2 of example 2, specifically results were given as follows:

comparative Sample 1: Lobaplatin obtained was amorphous;

comparative Sample 2: There were diffraction peaks at 2θ values of about 6.71, 8.35, 12.89, 15.14, 16.74, 17.45, 19.01, 19.40, 22.07, 22.76, 23.16, 24.30, 25.21, 25.74, 27.08, 30.26, 30.79 in the PXRD pattern by the X-ray diffraction, wherein the error range of 2θ values was less than 0.2. The melting point of this sample was described to be 210° C. (decomposition) in the patent EP 0611303.

Samples 1-12 in the present invention: there were diffraction peaks at 2θ values of about 8.25, 9.77, 11.70, 13.13, 15.28, 16.48, 17.22, 17.74, 19.01, 19.56, 22.28, 23.72, 24.04, 24.30, 25.62, 26.20, 28.57, 30.22, 30.61 in the PXRD pattern by the X-ray diffraction, wherein the error range of 2θ values was less than 0.2. There was an exothermal peak at 230±5° C. which was the melting and decomposition peak judged by combining with TGA datas and the melting point datas recorded in the European patent EP 0611303. All the datas showed that samples 1-12 had the same crystal form which was the new crystal form B of lobaplatin.

3. The Study of Solubility

Concentrations of 60 μg/ml, 80 μg/ml, 200 μm/ml, 400 μm/ml and 800 μm/ml lobaplatin trihydrate control solutions were prepared to make the standard curve by HPLC method. And the standard curve equation obtained was Y=4.8641X+20.5794, R=0.9998. Sample 1 of new crystal form B of lobaplatin and comparative sample 2 were prepared to be saturated aqueous solutions (suspensions) respectively. The solutions were vibrated in a shaker at 25° C. for 6 h followed by filtration, and diluted to appropriate multiples to be analyzed by HPLC. Solubility results were shown in Table 10 as follows:

TABLE 10

Study results of the solubility

| crystal form | sample 1 | comparative sample 1 |
|---|---|---|
| solubility (mg/ml) | 17.7341 | 10.3271 |

The results showed that: the solubility of lobaplatin compound prepared in the present invention was better than that of lobaplatin trihydrate.

4. The Quality Contrast Study of Lobaplatin New Crystal Forms 50 mg of samples 1-12 of lobaplatin compounds and comparative samples 1-2 were weighed respectively. Product moistures, impurities contents, contents of active ingredients, and yields were regarded as the indexes to study the product quality and yields. The theoretical moisture content of lobaplatin trihydrate is 11.96%. Results were shown in Table 11 below:

TABLE 11

The quality contrast study for the new lobaplatin crystal form B

| sample | moisture contents (%) | impurities contents (%) | lobaplatin contents (%, calculated in anhydrous lobaplatin) | yields (%) |
|---|---|---|---|---|
| sample 1 | 2.85 | 0.30 | 99.58 | 74 |
| sample 2 | 2.76 | 0.29 | 99.43 | 76 |
| sample 3 | 3.15 | 0.26 | 99.72 | 75 |
| sample 4 | 3.04 | 0.28 | 99.88 | 78 |
| sample 5 | 2.91 | 0.31 | 99.86 | 75 |
| sample 6 | 3.22 | 0.25 | 99.76 | 77 |
| sample 7 | 3.17 | 0.23 | 99.81 | 79 |
| sample 8 | 3.06 | 0.37 | 99.64 | 76 |
| sample 9 | 3.23 | 0.30 | 99.67 | 78 |
| sample 10 | 3.08 | 0.32 | 99.71 | 73 |
| sample 11 | 2.97 | 0.27 | 99.82 | 68 |
| sample 12 | 2.94 | 0.29 | 99.84 | 70 |
| comparative sample 1 | 3.78 | 1.21 | 98.26 | 64 |
| comparative sample 2 | 12.14 | 0.42 | 99.51 | 55 |

The above results showed that, compared with anhydrous lobaplatin and lobaplatin trihydrate, the new lobaplatin crystal form B obtained by the present invention had characteristics of high contents, low impurities and good yields.

Note 1: The determination method of contents: which was the same as that of the foregoing part 2.2 of example 2.

Note 2: The examination method of impurities: which was the same as that of the foregoing part 2.2 of example 2.

Note 3: The determination method of moisture contents: which was the same as that of the foregoing part 2.2 of example 2.

5. The Study of Stability

The sample 1 prepared in example 3 of the present invention and the prepared comparative sample 2 were respectively left to the conditions of a 60° C. oven, a relative humidity of about 95%, and a light stability test container of about 4500 lux illumination (a conventional incubator with the illumination function). The samples were taken out to perform PXRD tests and HPLC analyses after 5 days and 10 days to study the stability of samples under the condition of a high temperature, a high humidity and an illumination. Results are shown in table 12.

TABLE 12

| | The evaluation results of stability | | | | | |
|---|---|---|---|---|---|---|
| | Experimental conditions | | | | | |
| | thermo-stability | | wet stability | | light stability | |
| | sample 1 | comparative sample 2 | sample 1 | comparative sample 2 | Sample 1 | comparative sample 2 |
| PXRD 5 days | stable | stable | stable | stable | stable | stable |
| PXRD 10 days | stable | relatively stable | stable | relatively stable | stable | stable |
| HPLC 0 day | 99.877% | 99.513% | 99.877% | 99.513% | 99.854% | 99.513% |
| HPLC 5 days | 99.963% | 99.632% | 99.778% | 99.294% | 99.943% | 99.608% |
| HPLC 10 days | 99.962% | 98.737% | 99.930% | 98.815% | 99.937% | 98.726% |

The above mentioned experiment results showed that, the new lobplatin crystal form B in the present invention had a higher solubility than lobplatin trihydrate, and yields and purity were ideal. The new lobplatin crystal form B had a good stability and no appearance of crystal transformation phenomenon from the results of high temperature, high humidity and illumination study. Active ingredients's contents were superior to lobplatin trihydrate and had no apparent changes according to the HPLC results, indicating that the new lobplatin crystal form in the present invention was more stable than lobplatin trihydrate, not easy deliquescence to be sticky and had a good liquidity.

Example 4: Preparations of the New Lobaplatin Crystal Named Crystal Form F and Properties of the Product Thereof and Comparative Analyses 4.1 Preparations of New Lobaplatin Crystal Named Crystal Form F

Preparation Example 1 a. Preparations of lobaplatin dihydrate: 2 g of lobaplatin trihydrate were weighed and put in a container, and 30 ml of toluene were added in the container to obtain a suspension. The suspension was stirred for 48 h at room temperature, filtered, and the product obtained by filtering was washed with ethyl ether, and then 1.73 g of white powders were obtained after vacuum drying which was the lobaplatin dihydrate.

b. Preparations of the target crystal: 1 g of the lobaplatin dihydrate in step a were weighed and put in a container, and 40 ml of methanol were added in the container to obtain a mixture. The mixture was stirred at room temperature until solids were dissolved. The mixture was filtered to remove insolubles, and then 120 ml of ethylene glycol dimethyl ether were added slowly in the mixture to precipitate crystal. The crystal was filtered and separated. Then the crystal was washed with ethyl ether and 0.71 g of white powders were obtained after vacuum drying which was the new crystal form F of lobaplatin.

Preparation Example 2 a. Preparations of lobaplatin dihydrate: 2 g of lobaplatin trihydrate were weighed and put in a container, and 15 ml of methyl tertiary-butyl ether were added in the container to obtain a suspension. The suspension was stirred for 48 h at room temperature, filtered, and the product obtained by filtering was washed with ethyl ether, and then 1.84 g of white powders were obtained after vacuum drying which was the lobaplatin dihydrate.

b. Preparations of the target crystal: 1 g of the lobaplatin dihydrate in step a were weighed and put in a container, and 50 ml of methanol were added in the container to obtain a mixture. The mixture was stirred at room temperature until solids were dissolved. The mixture was filtered to remove insolubles, and then 150 ml of n-Hexane were added slowly in the mixture to precipitate crystal. The crystal was filtered and separated. Then the crystal was washed with ethyl ether and 0.68 g of white powders were obtained after vacuum drying which was the new crystal form F of lobaplatin.

Preparation Example 3 a. Preparations of lobaplatin dihydrate: 2 g of lobaplatin trihydrate were weighed and put in a container, and 20 ml of butyl acetate were added in the container to obtain a suspension. The suspension was stirred for 50 h at room temperature, filtered, and the product obtained by filtering was washed with ethyl ether, and then 1.68 g of white powders were obtained after vacuum drying which was the lobaplatin dihydrate.

b. Preparations of the target crystal: 1 g of the lobaplatin dihydrate in step a were weighed and put in a container, and 80 ml of ethanol were added in the container to obtain a mixture. The mixture was stirred at room temperature until solids were dissolved. The mixture was filtered to remove insolubles, and then 200 ml of ethyl acetate were added slowly in the mixture to precipitate crystal. The crystal was filtered and separated. Then the crystal was washed with ethyl ether and 0.70 g of white powders were obtained after vacuum drying which was the new crystal form F of lobaplatin.

Preparation Example 4 a. Preparations of lobaplatin dihydrate: 2 g of lobaplatin trihydrate were weighed and put in a container, and 25 ml of 1,4-dioxane were added in the container to obtain a suspension. The suspension was stirred for 45 h at room temperature, filtered, and the product obtained by filtering was washed with ethyl ether, and then 1.76 g of white powders were obtained after vacuum drying which was the lobaplatin dihydrate.

b. Preparations of the target crystal: 1 g of the lobaplatin dihydrate in step a were weighed and put in a container, and 90 ml of ethanol were added in the container to obtain a mixture. The mixture was stirred at room temperature until solids were dissolved. The mixture was filtered to remove insolubles, and then 180 ml of acetone were added slowly in the mixture to precipitate crystal. The crystal was filtered and separated. Then the crystal was washed with ethyl ether and 0.72 g of white powders were obtained after vacuum drying which was the new crystal form F of lobaplatin.

Preparation Example 5 a. Preparations of lobaplatin dihydrate: 2 g of lobaplatin trihydrate were weighed and put in a container, and 30 ml of n-heptane were added in the container to obtain a suspension. The suspension was stirred for 50 h at room temperature, filtered, and the product obtained by filtering was washed with ethyl ether, and then 1.75 g of white powders were obtained after vacuum drying which was the lobaplatin dihydrate.

b. Preparations of the target crystal: 1 g of the lobaplatin dihydrate in step a were weighed and put in a container, and 45 ml of methanol were added in the container to obtain a mixture. The mixture was stirred at room temperature until solids were dissolved. The mixture was filtered to remove insolubles, and then 160 ml of nitromethane were added slowly in the mixture to precipitate crystal. The crystal was filtered and separated. Then the crystal was washed with ethyl ether and 0.69 g of white powders were obtained after vacuum drying which was the new crystal form F of lobaplatin.

Preparation Example 6 a. Preparations of lobaplatin dihydrate: 2 g of lobaplatin trihydrate were weighed and put in a container, and 15 ml of ethyl ether were added in the container to obtain a suspension. The suspension was stirred for 48 h at room temperature, filtered, and the product obtained by filtering was washed with ethyl ether, and then 1.78 g of white powders were obtained after vacuum drying which was the lobaplatin dihydrate.

b. Preparations of the target crystal: 1 g of the lobaplatin dihydrate in step a were weighed and put in a container, and 40 ml of methanol were added in the container to obtain a mixture. The mixture was stirred at room temperature until solids were dissolved. The mixture was filtered to remove insolubles, and then 150 ml of acetonitrile were added slowly in the mixture to precipitate crystal. The crystal was filtered and separated. Then the crystal was washed with ethyl ether and 0.73 g of white powders were obtained after vacuum drying which was the new crystal form F of lobaplatin.

Preparation Example 7 a. Preparations of lobaplatin dihydrate: 2 g of lobaplatin trihydrate were weighed and put in a container, and 15 ml of methyl tertiary-butyl ether were added in the container to obtain a suspension. The suspension was stirred for 48 h at room temperature, filtered, and the product obtained by filtering was washed with ethyl ether, and then 1.84 g of white powders were obtained after vacuum drying which was the lobaplatin dihydrate.

b. Preparations of the target crystal: 1 g of the lobaplatin dihydrate in step a were weighed and put in a container, and 85 ml of ethanol were added in the container to obtain a mixture. The mixture was stirred at room temperature until solids were dissolved. The mixture was filtered to remove insolubles, and then 180 ml of tetrahydrofuran were added slowly in the mixture to precipitate crystal. The crystal was filtered and separated. Then the crystal was washed with ethyl ether and 0.67 g of white powders were obtained after vacuum drying which was the new crystal form F of lobaplatin.

Preparation Example 8 a. Preparations of lobaplatin dihydrate: 2 g of lobaplatin trihydrate were weighed and put in a container, and 20 ml of methyl tertiary-butyl ether were added in the container to obtain a suspension. The suspension was stirred for 46 h at room temperature, filtered, and the product obtained by filtering was washed with ethyl ether, and then 1.80 g of white powders were obtained after vacuum drying which was the lobaplatin dihydrate.

b. Preparations of the target crystal: 1 g of the lobaplatin dihydrate in step a were weighed and put in a container, and 40 ml of methanol were added in the container to obtain a mixture. The mixture was stirred at room temperature until solids were dissolved. The mixture was filtered to remove insolubles, and then 150 ml of dichlormethane were added slowly in the mixture to precipitate crystal. The crystal was filtered and separated. Then the crystal was washed with ethyl ether and 0.66 g of white powders were obtained after vacuum drying which was the new crystal form F of lobaplatin.

The samples prepared according to step a) in the above mentioned preparation examples 1-8 were measured with XRD diffraction by the method of 1.4 in the foregoing example 1. All the 8 samples were determined to have the same crystal form which was crystal form A. And the detailed determination datas were the same as these of the foregoing first part of the embodiment which was "a first embodiment of the present invention" and these of the foregoing example 2.

On the other hand, the samples prepared in the above mentioned preparation examples 1-8 by the method of 1.4 of example 1 were measured with the XRD diffraction. All the 8 samples were determined to have the same crystal form, and the characteristic peaks were as follows: there were diffraction peaks at 2θ values of about 8.21, 11.60, 12.99, 15.24, 16.44, 17.11, 17.55, 18.42, 19.01, 19.20, 19.42, 21.81, 22.17, 22.42, 23.33, 23.85, 24.18, 24.40, 24.77, 25.46, 25.98, 26.13, 27.89, 28.42, 29.03, 30.32, 31.17, 31.94, 33.30, 36.20, 37.62, 39.66 in the PXRD pattern, wherein the error range of 2θ values was ±0.2. This crystal form was named as crystal form F.

4.2 Properties Determination for Products of Crystal Form F and Comparative Analyses Thereof 1. Test Samples Samples 1-8: prepared by the method of preparation examples 1-8 respectively in the present invention.

Comparative sample 1: which was the same as the foregoing sample of comparative sample 1 in part 2.2 of example 2. The lobaplatin prepared according to the method of example 1a in the patent EP0324154, and the specific preparation methods were the same as these of the foregoing comparative sample 1 in part 2.2 of example 2.

Comparative sample 2: which was the same as the foregoing sample of comparative samples 2 in part 2.2 of example 2. The lobaplatin was prepared according to the method of example in the patent EP0611303, and the specific preparation methods were the same as these of the foregoing comparative sample 2 in part 2.2 of example 2.

2. Morphological Identifications

The identification results were the same as comparative sample 1 and comparative sample 2 in part 2.2 of example 2, specifically results were given as follows:

Comparative Sample 1: Lobaplatin obtained was amorphous;

Comparative Sample 2: There were diffraction peaks at 2θ values of about 6.71, 8.35, 12.89, 15.14, 16.74, 17.45, 19.01, 19.40, 22.07, 22.76, 23.16, 24.30, 25.21, 25.74, 27.08, 30.26, 30.79 in the PXRD pattern by the X-ray diffraction, wherein the error range of 2θ values was less than 0.2. The melting point of this sample was described to be 210° C. (decomposition) in the patent EP0611303.

Samples 1-8 in the present invention: there were diffraction peaks at 2θ values of about 8.21, 11.60, 12.99, 15.24, 16.44, 17.11, 17.55, 18.42, 19.01, 19.20, 19.42, 21.81, 22.17, 22.42, 23.33, 23.85, 24.18, 24.40, 24.77, 25.46, 25.98, 26.13, 27.89, 28.42, 29.03, 30.32, 31.17, 31.94, 33.30, 36.20, 37.62, 39.66 in the PXRD pattern by the X-ray diffraction, wherein the error range of 2θ values was less than 0.2. There was an exothermal peak near 229° C. in the DSC pattern which was the melting and decomposition peak judged by combining with TGA datas and the melting point datas recorded in the European patent EP 0611303. All the datas showed that samples 1-8 had the same crystal form which was the new crystal form F of lobaplatin.

3. The Study of Solubility

Concentrations of 60 μg/ml, 80 μg/ml, 200 μm/ml, 400 μm/ml and 800 μm/ml lobaplatin trihydrate control solutions were prepared to make the standard curve by HPLC method. And the standard curve equation obtained was Y=4.8641X+20.5794, R=0.9998. Sample 6 of new lobaplatin crystal and comparative sample 2 were prepared to be saturated aqueous solutions (suspensions) respectively. The solutions were vibrated in a shaker at 25° C. for 6 h followed by filteration, and diluted to appropriate multiples to be analyzed by HPLC. The solubility results were shown in Table 13 as follows:

TABLE 13

The solubility results of solubility

| crystal form | sample 6 | comparative sample 1 |
|---|---|---|
| solubility (mg/ml) | 21.4957 | 10.3271 |

The results showed that: the solubility of lobaplatin compound prepared in the present invention was better than that of lobaplatin trihydrate.

4. The Quality Contrast Study of Lobaplatin New Crystal Forms 20 mg of samples 1-8 of lobaplatin dihydrate and comparative sample 1-2 were weighed respectively. Product moistures, impurities contents, contents of active ingredients, and yields were regarded as the indexes to study the product quality and yields. Results were shown in Table 14 below:

TABLE 14

The quality contrast study for new lobaplatin crystal

| sample | moisture contents (%) | impurities contents (%) | lobaplatin contents (%, calculated on anhydrous lobaplatin) | yields (%) |
|---|---|---|---|---|
| sample 1 | 1.98 | 0.15 | 99.91 | 71 |
| sample 2 | 2.12 | 0.17 | 99.85 | 68 |
| sample 3 | 2.07 | 0.20 | 99.93 | 70 |
| sample 4 | 1.95 | 0.16 | 99.90 | 72 |
| sample 5 | 2.11 | 0.21 | 99.88 | 69 |
| sample 6 | 2.03 | 0.14 | 99.96 | 73 |
| sample 7 | 2.09 | 0.16 | 99.89 | 67 |
| sample 8 | 1.91 | 0.18 | 99.92 | 66 |
| comparative sample 1 | 3.78 | 1.21 | 98.26 | 64 |
| comparative sample 2 | 12.14 | 0.42 | 99.51 | 55 |

The above mentioned results showed that, compared with anhydrous lobaplation and lobaplatin trihydrate, the new lobaplatin crystal form F obtained by the present invention characteristics of high contents, low impurities, and good yields.

Note 1: The determination method of contents: which was the same as the foregoing part 2.2 of example 2.

Note 2: The examination method of impurities: which was the same as the foregoing part 2.2 of example 2.

Note 3: The determination method of moisture contents: which was the same as the foregoing part 2.2 of example 2.

5. The Study of Stability

The sample 6 prepared in the example of the present invention and the prepared comparative sample 2 were respectively left to the conditions of a 60° C. oven, a relative humidity of about 95%, and a light stability test container of about 4500 lux illumination (a conventional incubator with the illumination function). The samples were taken out to perform PXRD tests and HPLC analyses after 5 days and 10 days to study the stability of samples under the condition of a high temperature, a high humidity and an illumination. Results are shown in table 15.

TABLE 15

The evaluation results of stability

| | Experimental conditions | | | | | |
|---|---|---|---|---|---|---|
| | thermo-stability | | wet stability | | light stability | |
| | sample 6 | comparative sample 2 | sample 6 | comparative sample 2 | sample 6 | comparative sample 2 |
| PXRD 5 days | stable | stable | stable | stable | stable | Stable |
| PXRD 10 days | stable | relatively stable | stable | relatively stable | stable | stable |
| HPLC 0 days | 99.959% | 99.513% | 99.959% | 99.513% | 99.959% | 99.513% |

TABLE 15-continued

The evaluation results of stability

| | Experimental conditions | | | | | |
|---|---|---|---|---|---|---|
| | thermo-stability | | wet stability | | light stability | |
| | sample 6 | comparative sample 2 | sample 6 | comparative sample 2 | sample 6 | comparative sample 2 |
| HPLC 5 days | 99.850% | 99.632% | 99.963% | 99.294% | 99.913% | 99.608% |
| HPLC 10 days | 99.961% | 98.737% | 99.904% | 98.815% | 99.934% | 98.726% |

The above mentioned experiment results showed that, the new lobplatin crystal form F in the present invention had a higher solubility than lobplatin trihydrate, and yields and purity were ideal. The new lobplatin crystal form F had a good stability and no appearance of crystal transformation phenomenon from the results of a high temperature, a high humidity and an illumination study. Active ingredients' contents were superior to lobplatin trihydrate and had no apparent changes according to the HPLC results, indicating that the new lobplatin crystal was stable.

The invention claimed is:

1. A lobaplatin compound crystal is characterized in two molecules of crystal water existing in a crystal structure.

2. The lobaplatin compound crystal according to claim 1, wherein, a crystal form of said lobaplatin compound is crystal form A, and there are diffraction peaks at 2θ values of about 11.04, 12.32, 12.61, 13.85, 15.14, 15.55, 16.68, 17.67, 17.86, 19.03, 20.06, 21.00, 22.68, 22.92, 23.76, 25.39, 25.58, 26.37, 26.77, 27.00, 27.71, 28.13, 29.71, 31.42, 31.94, 32.89, 34.29, 34.60, 36.10, 36.93, 37.66, 40.78, 43.41 in a PXRD pattern, wherein an error range of 2θ values is 0.2.

3. The lobaplatin compound crystal according to claim 2, wherein, a melting point Tm.p. of said lobaplatin compound crystal is 220±5° C.

4. A lobaplatin compound crystal is characterized in that a crystal form of said lobaplatin compound is crystal form B, and there are diffraction peaks at 2θ values of about 8.25, 9.77, 11.70, 13.13, 15.28, 16.48, 17.22, 17.74, 19.01, 19.56, 22.28, 23.72, 24.04, 24.30, 25.62, 26.20, 28.57, 30.22, 30.61 in a PXRD pattern, wherein an error range of 2θ values is 0.2.

5. The lobaplatin compound crystal according to claim 4, is characterized in that a melting point Tm.p. of said lobaplatin compound crystal is 230±5° C.

6. A lobaplatin compound crystal is characterized in that a crystal form of the compound crystal is crystal form F, and there are diffraction peaks at 2θ values of about 8.21, 11.60, 12.99, 15.24, 16.44, 17.11, 17.55, 18.42, 19.01, 19.20, 19.42, 21.81, 22.17, 22.42, 23.33, 23.85, 24.18, 24.40, 24.77, 25.46, 25.98, 26.13, 27.89, 28.42, 29.03, 30.32, 31.17, 31.94, 33.30, 36.20, 37.62, 39.66 in a PXRD pattern, wherein an error range of 2θ values is 0.2.

7. The lobaplatin crystal according to claim 6 is characterized in that a melting point Tm.p. of said lobaplatin compound crystal is 229±5° C.

* * * * *